(12) United States Patent
Boussie et al.

(10) Patent No.: US 10,017,486 B2
(45) Date of Patent: Jul. 10, 2018

(54) CONVERSION OF FRUCTOSE-CONTAINING FEEDSTOCKS TO HMF-CONTAINING PRODUCT

(71) Applicant: Archer-Daniels-Midland Company, Decatur, IL (US)

(72) Inventors: Thomas R. Boussie, Menlo Park, CA (US); Eric L. Dias, Belmont, CA (US); Vincent J. Murphy, San Jose, CA (US); James A. W. Shoemaker, Gilroy, CA (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 15/437,570

(22) Filed: Feb. 21, 2017

(65) Prior Publication Data

US 2017/0158656 A1    Jun. 8, 2017

Related U.S. Application Data

(62) Division of application No. 14/606,789, filed on Jan. 27, 2015, now Pat. No. 9,611,241.

(60) Provisional application No. 61/932,185, filed on Jan. 27, 2014.

(51) Int. Cl.
C07D 307/46    (2006.01)

(52) U.S. Cl.
CPC ................. C07D 307/46 (2013.01)

(58) Field of Classification Search
None
See application file for complete search history.

(56) References Cited

U.S. PATENT DOCUMENTS

| | | | |
|---|---|---|---|
| 2,750,394 A | 6/1956 | Peniston | |
| 2,754,330 A | 7/1956 | Schreyer | |
| 2,917,520 A | 12/1959 | Cope | |
| 2,929,823 A | 3/1960 | Garber et al. | |
| 3,118,912 A | 1/1964 | Smith | |
| 4,339,387 A | 7/1982 | Fleche | |
| 4,400,468 A | 8/1983 | Faber | |
| 4,533,743 A | 8/1985 | Madeiros et al. | |
| 4,590,283 A | 5/1986 | Gaset et al. | |
| 4,740,605 A | 4/1988 | Rapp | |
| 4,912,237 A | 3/1990 | Zeitsch | |
| 4,971,657 A | 11/1990 | Avignon et al. | |
| 6,518,440 B2 | 2/2003 | Lightner | |
| 6,743,928 B1 | 6/2004 | Zeitsch | |
| 7,572,925 B2 | 8/2009 | Dumesic et al. | |
| 7,579,490 B2 | 8/2009 | Sanborn et al. | |
| 8,058,458 B2 | 11/2011 | Sanborn | |
| 8,242,293 B2 | 8/2012 | Gruter et al. | |
| 8,604,225 B2 | 12/2013 | Pedersen et al. | |
| 8,772,515 B2 | 7/2014 | Dumesic et al. | |
| 9,090,579 B2 | 7/2015 | Binder et al. | |
| 9,199,957 B2 | 12/2015 | Siqueira et al. | |
| 9,206,148 B2 | 12/2015 | Cho et al. | |
| 9,238,635 B2 | 1/2016 | Essayem et al. | |
| 2010/0004437 A1 | 1/2010 | Binder et al. | |
| 2010/0317822 A1 | 12/2010 | Boussie et al. | |
| 2013/0184495 A1 | 7/2013 | Dias et al. | |
| 2014/0315262 A1 | 10/2014 | Sanborn et al. | |

FOREIGN PATENT DOCUMENTS

| | | |
|---|---|---|
| AU | 2011205116 A1 | 8/2011 |
| CA | 2097821 C | 6/1992 |
| CA | 2856466 A1 | 6/2013 |
| EP | 2390247 A1 | 11/2011 |
| FR | 2669635 B1 | 11/1990 |
| FR | 2663933 A1 | 1/1992 |
| FR | 2664273 A1 | 1/1992 |
| GB | 591858 A1 | 9/1947 |
| GB | 600871 A1 | 4/1948 |
| GB | 876463 A1 | 9/1961 |
| WO | 92010486 A1 | 12/1991 |
| WO | 2011149339 A1 | 1/2011 |
| WO | 2012156479 A1 | 3/2013 |
| WO | 2013034763 A1 | 3/2013 |
| WO | 2013053816 A1 | 4/2013 |
| WO | 2013106136 A1 | 7/2013 |
| WO | 2013133489 A1 | 9/2013 |
| WO | 2014037560 A1 | 3/2014 |
| WO | 2014152366 A1 | 9/2014 |

OTHER PUBLICATIONS

Hu, L. et al., "Advances in Production of 5-Hyrdroxymethylfurfural from Glucose," 2011, Chem Ind and Eng Prog, 30/8:1711-1716, 6 pages. English abstract only.
Tucker, M.H., et al, "Acid-Functionalized SBA-15-Type Periodic Mesoporous Organosilicas and Their Use in the Continuous Production of 5-Hydroxymethylfurfural," 2012, ACS Catalysis, 2:1865-1876.
Tucker, M.H. et al., Supporting Documentation for Acid-Functionalized SBA-15-Type Periodic Mesoporous Organosilicas and their Use in the Continuous Production of 5-Hydroxymethylfurfural, 2012,15 Pages.
van Putten, R-J., et al., "Hydroxymethylfurfural, a Versatile Platform Chemical Made from Renewable Resources," 2013, Chem Rev, 113:1499-1597.
Aiken, G.R., et al., "Molecular Mapping of the Acid Catalysed Dehydration of Fructose," 2012, Chem Commun, 48:5850-5852.
Aiken, G.R., et al., "Molecular Mapping of the Acid Catalysed Dehydration of Fructose," Electronic Supplementary Information, "Experimental," 2012, Chem Commun, Royal Soc of Chem, 10 pages.

(Continued)

*Primary Examiner* — Kristin A Vajda
(74) *Attorney, Agent, or Firm* — Senniger Powers LLP

(57) ABSTRACT

The present invention relates generally to processes for converting fructose-containing feedstocks to a product comprising 5-(hydroxymethyl)furfural (HMF) and water in the presence of water, solvent and an acid catalyst. In some embodiments, the conversion of fructose to HMF is controlled at a partial conversion endpoint characterized by a yield of HMF from fructose that does not exceed about 80 mol %. In these and other embodiments, the processes provide separation techniques for separating and recovering the product, unconverted fructose, solvent and acid catalyst to enable the effective recovery and reutilization of reaction components.

18 Claims, 9 Drawing Sheets

(56) References Cited

OTHER PUBLICATIONS

Kazi, F.K. et al., "Techno-economic Analysis of Dimethylfuran (DMF) and Hydroxymethylfurfural (HMF) Production from Pure Fructose in Catalytic Processes," 2011, Chem Eng J, 169:329-338.
Szmant, H.H., et al., "The Preparation of 5-Hydroxymethylfurfuraldehyde from High Fructose Corn Syrup and Other Carbohydrates," 1981, J Chem Tech Biotech, 31/1:135-145, Abstract only.
Werpy, T; Petersen, G. (Eds.), "Top Value Added Chemicals from Biomass, vol. 1: Results of Screening for Potential Candidates from Sugars and Synthesis Gas," U.S. Dept. of Energy, Office of Scientific Information: Oak Ridge, Tenn. DOE/GO-102004-1992 (2004).
Membrane Filtration Guidance Manual, U.S. EPA, Office of Water, EPA 815-R-06-009, Nov. 2005, 332 pages.
Invitation to Pay Additional Fees dated Mar. 31, 2015 in PCT/US2015/013130.
International Search Report issued in PCT/US2015/013130 dated Sep. 21, 2015.

CONVERSION OF FRUCTOSE-CONTAINING FEEDSTOCKS TO HMF-CONTAINING PRODUCT

CROSS-REFERENCE TO RELATED APPLICATIONS

This application is a division of U.S. application Ser. No. 14/606,789, filed Jan. 27, 2015, which claims benefit of U.S. provisional application Ser. No. 61/932,185, filed Jan. 27, 2014, the entire disclosures of which are incorporated herein by reference.

FIELD OF THE INVENTION

The present invention relates generally to processes for converting fructose-containing feedstocks, for example, high fructose corn syrup-containing feedstocks, to a product comprising 5-(hydroxymethyl)furfural (HMF) and water. In one aspect of the invention, the process comprises the step of converting a fructose-containing feedstock to HMF in a reaction zone in the presence of water, solvent and acid catalyst to attain a relatively low specified yield of HMF at a partial conversion endpoint and thereafter the conversion of fructose to HMF is quenched at the partial conversion endpoint. Typically, the sum of unconverted fructose, HMF yield, and the yield of intermediates is at least 90 mol % at the partial conversion endpoint. In another aspect of the invention, the process comprises partially converting the feedstock in a reaction zone in the presence of water, solvent and an acid catalyst, removing from the reaction zone the combination resulting from the partial conversion, separating unconverted fructose from the reaction combination removed from the reaction zone, and separating solvent separately from the separation of the unconverted fructose, the separations being conducted to enable the subsequent recovery of product comprising HMF and water. The post reaction zone separations also enable the effective recovery and reutilization of unconverted fructose and solvent. In another aspect of the invention, selective membrane separation techniques are employed for the separation and recovery of unconverted fructose and intermediates from the desired product.

BACKGROUND OF THE INVENTION

HMF has been recognized as a chemical with potentially significant industrial and commercial applications because of its high degree of functionality and its ability to act as a precursor to various industrially useful chemicals. See Werpy, T; Petersen, G. (Eds.), *"Top Value Added Chemicals from Biomass,* Vol. 1: *Results of Screening for Potential Candidates from Sugars and Synthesis Gas,"* U.S. Dept. of Energy, Office of Scientific Information: Oak Ridge, Tenn. DOE/GO-102004-1992 (2004). For example, its functionality affords use in the production of solvents, surfactants, pharmaceuticals and plant protecting agents, and furan derivatives thereof which are useful as monomers for the preparation of non-petroleum derived polymers.

HMF is primarily produced by dehydrating a carbohydrate feedstock, particularly monosaccharides such as glucose and fructose. Complications commonly arise during the reaction as a result of the production of unwanted acid by-products, particularly levulinic and formic acid, and especially the polymerization of reaction components which forms humins (a mixture of colored, soluble and insoluble oligomers and polymers), all of which reduce the overall process yield and complicate the recovery of HMF, making large scale production of HMF economically unattractive. These complications are exacerbated by the desire to maximize conversion of feedstock to HMF in the reaction zone.

Fructose is the preferred hexose to produce HMF because it has been demonstrated to be more amenable to dehydration reactions than other hexoses including glucose. High fructose corn syrup (HFCS) is a high volume, commercially available product from which HMF and other furans could be produced in large quantities. Currently, as much as 18 billion pounds/yr of high fructose corn syrup are produced. Szmant et al, J. Chem. Tech. Biotechnology, Vol. 31, PP 135-45 (1981) disclosed the use of high fructose corn syrup as a feedstock for the production of HMF.

A variety of homogeneous catalysts have been employed to promote the dehydration of fructose to HMF. Inexpensive strong inorganic acids have been used: see, for example, U.S. Pat. No. 7,572,925. Organic acids have also been disclosed, including relatively strong organic acids such as p-toluene sulfonic acid and weaker organic acids such as oxalic acid and levulinic acid: See, for example, U.S. Pat. No. 4,740,605, which discloses oxalic acid. All patents and other publications cited in this application are incorporated herein by reference.

Similarly, a variety of heterogeneous catalysts have been reported as useful for the dehydration of carbohydrate to HMF. See, for example de Vries, Chem. Rev. 2013, pp1499-1597. Dumesic, ACS Catal 2012, 2, pp1865-1876; and Sandborn, U.S. Pat. No. 8,058,458. Fleche, in U.S. Pat. No. 4,339,387, disclosed the use of solid acid resin catalysts where the resin may be a strong or weak cationic exchanger, with the functionalization preferably being in the $H^+$ form (including, for example, resins under the trademark Amberlite C200 from Rohm & Haas Corporation and Lewatit SPC 108 from Bayer AG). Sanborn, in AU 2011205116, disclosed that metals such as Zn, Al, Cr, Ti, Th, Zr and V are useful as catalysts. And Binder, in US 2010/0004437 A1, disclosed the use of a halide salt.

In addition to the use of catalysts in the dehydration of carbohydrates to HMF, there has been much focus on solvents and solvent systems that reportedly are beneficial in the process. See for example, de Vries Chem. Rev 2013, 113, 1499-1597.

A multitude of processes have been disclosed for the production of HMF from fructose. However, the known prior processes have not recognized any benefit associated with low conversion in the reaction zone. Typically, research has focused on attaining the highest possible conversion of fructose to HMF in the reaction zone, which inevitably has resulted in increased off-path products, including humins, and/or process complexity and expense. In the quest to attain high conversion of fructose to HMF in the reaction zone, prior processes have focused on improving catalyst performance, reactor solvent systems and reactant mixing techniques, using solvent modifiers to improve phase separations in the reactor, using foam and/or oxidation suppressants, reducing carbohydrate concentration in the reactor, using very high temperatures and/or pressures, and performing multiple steps in the reactor (e.g., steam injection or controlled vaporization to simultaneously remove certain constituents), among other techniques. Nevertheless, none of the processes disclosed to date appears to have overcome the low overall process productivity in a commercially economically viable manner.

In order to overcome the shortcomings of the prior processes, applicants have discovered processes based upon intentionally limiting the conversion of fructose to HMF in the reaction zone. In these processes, HMF, unconverted fructose, solvent and, when applicable, catalyst are removed from the reaction zone and ultimately separated from one another, enabling the efficient recycling of these separated constituents and, ultimately, the cost effective production and recovery of large quantities of HMF.

SUMMARY OF THE INVENTION

Briefly, therefore, the present invention is directed to improved processes for converting fructose-containing feedstocks to a product comprising HMF and water.

In one embodiment, the process comprises combining fructose, water, an acid catalyst and a first solvent in a reaction zone and converting in the reaction zone fructose to HMF and water and to intermediates to HMF to a partial conversion endpoint. The yield of HMF from fructose at the partial conversion endpoint does not exceed about 80 mol %. At least a portion of the product, unconverted fructose and the first solvent are removed from the reaction zone, as a combination, wherein the conversion of fructose to HMF in the combination removed from the reaction zone is quenched at the partial conversion endpoint. At least a portion of each of the first solvent, the product and unconverted fructose in the combination removed from the reaction zone are separated from one another. At least a portion of the separated unconverted fructose and at least a portion of the separated first solvent are subsequently recycled to the reaction zone and the product comprising HMF and water is recovered.

In accordance with another embodiment, the process comprises combining fructose, water, an acid catalyst and at least a first solvent in a reaction zone and converting in the reaction zone a portion of the fructose to HMF and water. At least a portion of the product, unconverted fructose and the first solvent are removed from the reaction zone as a combination and at least a portion of the combination is contacted with a second solvent in a fructose separator to separate at least a portion of unconverted fructose from the combination and produce an intermediate composition having a reduced fructose concentration and comprising the product and at least a portion of each of the first solvent and second solvent. At least a portion of the separated, unconverted fructose is recovered and at least a portion of the first solvent, the second solvent and the product in the intermediate composition are separated from one another.

In accordance with a further embodiment, the process comprises combining fructose, water, an acid catalyst and at least a first solvent in a reaction zone and converting in the reaction zone a portion of the fructose to HMF and water and to intermediates to HMF. At least a portion of the product, unconverted fructose, intermediates and first solvent are removed from the reaction zone as a combination and one or more constituents of the combination withdrawn from the reaction zone are separated by selective membrane separation.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
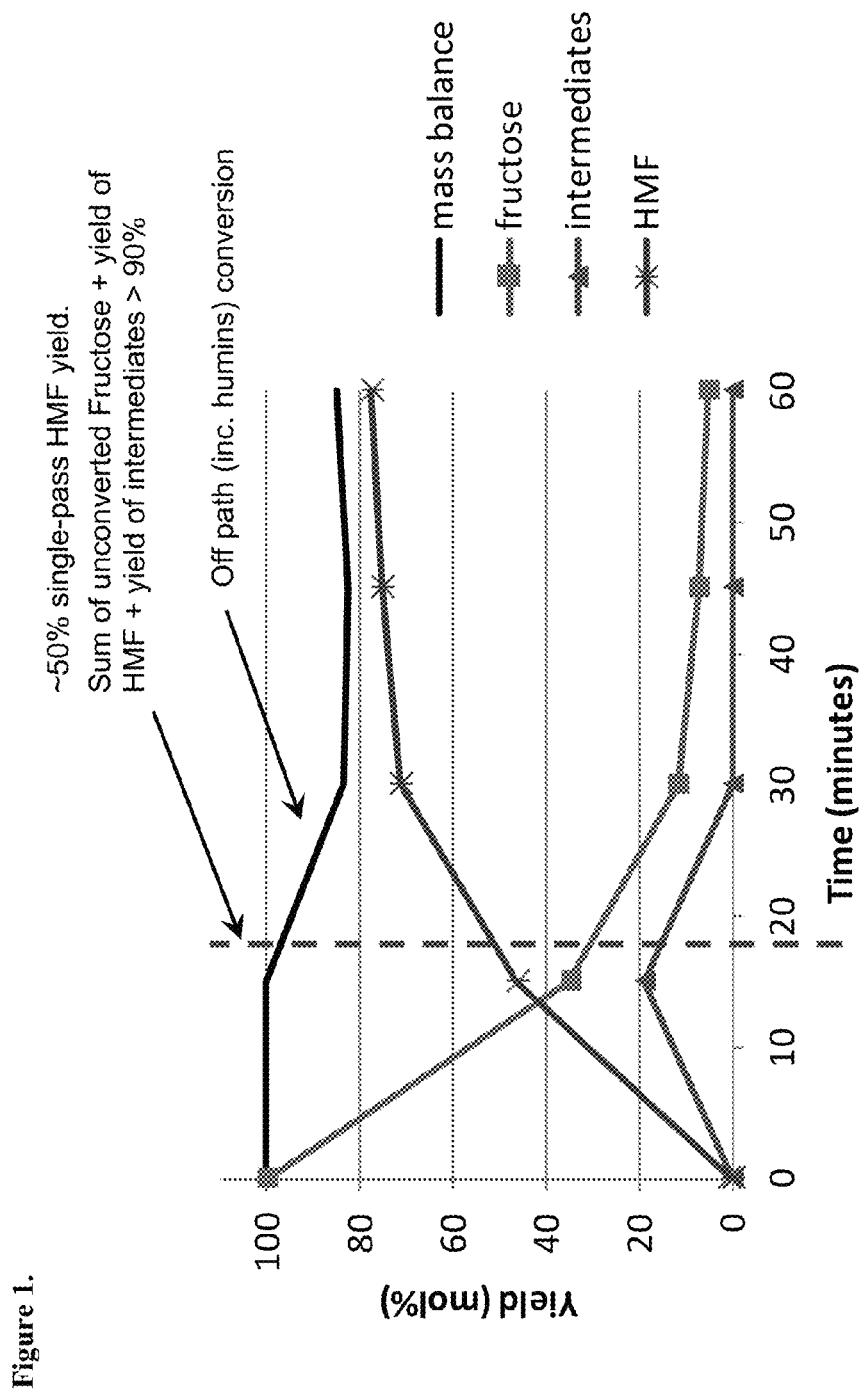
FIG. 1 graphically illustrates a typical conversion of fructose to HMF in a reaction zone as a function of time, highlighting changes in fructose, HMF and intermediate concentrations as well as changes in reaction mass balance, the latter of which is reflective of an increased concentration of off-path reaction products (including humins) at higher fructose conversions.

In accordance with the present invention, any of a variety of fructose-containing feedstocks can be employed including, without limitation, essentially pure fructose, sucrose, mixtures of glucose and fructose, and combinations thereof. Moreover, the present invention contemplates the use of starches, cellulosics and other forms of carbohydrates which, for example, are subjected to processing conditions that isomerize glucose produced from the starches or cellulosics to form fructose-containing feedstocks.

An aspect of the present invention is the partial conversion of a fructose-containing feedstock to HMF. The conversion is carried out in a reaction zone that contains at least fructose-containing feedstock, water, acid catalyst and solvent.

Water can be present in a reaction zone either as a separately added constituent or as a component of, for example, a solution of fructose-containing feedstock. Conjunctively or alternatively, and without limiting the scope of the invention, water may be present in a reaction zone as a solution comprised of a reaction modifier, such as an aqueous salt solution, as more fully described hereinafter.

Typically, an aqueous solution of fructose is used as the feedstock to the reaction zone. In various preferred embodiments, commercially available high fructose corn syrup (HFCS) is dissolved in water to form the solution. For example, HFCS-97 or HFCS-90 may be used.

The concentration of fructose in a reaction zone is generally in the range of from about 5 wt % to about 80 wt % dissolved solids. In various embodiments, the concentration of dissolved solids is in the range of about 20 wt % to about 80 wt %. In various embodiments, the concentration of dissolved solids is at least about 40 wt %. In some embodiments, it may be desirable to lower the concentration of fructose in the solutions to 20 wt % or less.

In accordance with the present invention the reaction takes place in a reaction zone in the presence of an acid catalyst. The catalyst may be a homogeneous or heterogeneous catalyst. Homogeneous catalysts include Brnsted or Lewis acids. Examples of such acids include organic and inorganic acids. Inorganic acids include mineral acids and other strong acids. Brnsted acids include HCl, HI, $H_2SO_4$, $HNO_3$, $H_3PO_4$, oxalic acid $CF_3SO_3H$ and $CH_3SO_3H$. Lewis acids can include for example, borontrihalides, organoboranes, aluminum trihalides, phosphorus and antimony pentafluorides, rare earth metal triflates, and metal cation ether complexes. Preferred acids are Brnsted acids selected from the group of HCl, HBr, $H_2SO_4$ and $H_3PO_4$. Quantities of catalyst when homogeneous are typically in the range of from about 0.1 to about 25 mol. % vs. hexose, more typically from about 0.5 to about 10 mol. % or from about 0.5 to about 5 mol. %. Suitable heterogeneous catalysts include acid-functionalized resins, acidified carbons, zeolites, micro- and meso-porous metal oxides, sulfonated and phosphonated metal oxides, clays, polyoxometallates and combinations thereof. Preferred heterogeneous catalysts include acid functionalized resins. When a heterogeneous catalyst is employed, the catalyst loading in the reaction mixture will depend upon the type of reactor utilized. For example, in a slurry reactor, the catalyst loading may range from about 1 g/L to about 20 g/L; in a fixed bed reactor the catalyst loading may range from about 200 g/L to about 1500 g/L.

Also present in the reaction zone is a solvent. Solvents are typically organic solvents and can either be polar or non-polar solvents. Generally, useful solvents can be selected from among ethers, alcohols, ketones and hydrocarbons. Examples of useful solvents include ethers such diethyl ether, methyl tert-butyl ether, dimethoxyethane (DME or glyme), bis(2-methoxyethyl) ether (diglyme), tetrahydrofuran (THF), dioxane, and 2-methyltetrahydrofuran (MeTHF), ketones such as acetone, methyl ethyl ketone and methyl isobutyl ketone (MIBK), alcohols such as isopropanol, 2-butanol, and tert-butanol, and hydrocarbons such as pentane, hexane, cyclohexane and toluene. In various embodiments, solvents include DME, dioxane, THF, MeTHF, 2-butanol, and MIBK.

The fructose-containing feedstock, water, catalyst and solvent can exist in the reaction zone as a mono- or multi-phasic system. The amount of solvent in the system relative to water typically ranges from 10:1 to 1:1 on a mass basis. In various embodiments it can range from 5:1 to 2:1. The presence of organic solvent in the reaction zone promotes both faster reaction rates and higher yields of HMF. Solvent-water combinations that form either mono- or multi-phasic compositions in the reaction zone can be employed. Preferred solvents for the reaction zone are unreactive under the conditions of fructose dehydration, and have boiling points lower than water.

An important aspect of the invention is the partial conversion of the fructose in the reaction zone. That is, the dehydration reaction is allowed to proceed until a partial conversion endpoint is attained and then the reaction is at least partially quenched (i.e., the conversion of fructose is reduced). In accordance with the present invention, the conversion of fructose in the reaction zone is controlled such that at the partial conversion endpoint, the yield of HMF from fructose provided to the reaction zone is maintained at a relatively low specified yield. As discussed in greater detail below, applicants have discovered that controlling the conversion of fructose to HMF at a specified yield reduces conversion of HMF and/or fructose to off-path products such as oligomers and polymers produced from the reaction components and referred to herein as humins, especially those which are soluble in water or the solvent supplied to the reaction zone.

FIG. 1 graphically illustrates a typical conversion of fructose to HMF in a reaction zone as a function of time, highlighting changes in fructose, HMF and intermediate concentrations as well as changes in reaction mass balance, the latter of which is reflective of an increased concentration of off-path reaction products (e.g., levulinic acid, formic acid, and soluble and insoluble humins) at higher fructose conversions. Mass balance in this instance is defined as the sum of unconverted fructose plus the mol % yield of HMF plus the mol % yield of reaction intermediates. As discussed by István T Horvath et al. (*Molecular Mapping of the Acid-Catlaysed Dehydration of Fructose*, Chem. Commun., 2012, 48, 5850-5852), several different reaction pathways exist for the conversion of fructose to HMF as well as the generation of various off-path products that are believed to lead to the formation of humins. On-path intermediates to HMF are reported to include isomers of fructose such as α-D-fructofuranose and β-D-fructofuranose, 2,6-anhydro-β-D-fructofuranose, fructofuranosyl oxocarbenium ions, (2R,3S,4S)-2-(hydroxymethyl)-5-(hydroxyl-methylene)-tetrahydrofuran-3,4-diol, (4S,5R)-4-hydroxy-5-hydroxymethyl-4,5-dihydrofuran-2-carbaldehyde and difructose dianhydrides (DFAs). Off-path intermediates are reported to include (3S,4R,5R)-2-(hydroxymethylene)-tetrahydro-2H-pyran-3,4,5-triol and (3R,4S)-3,4-dihydroxy-3,4-dihydro-2H-pyran-6-carbaldehyde, which can be converted to humins.

FIG. 1 also graphically depicts a typical conversion of fructose-containing feedstock to HMF in accordance with the present invention, highlighting certain of the benefits attributable to partial conversion to HMF. More specifically, at time zero, no conversion occurs. At time "t" (represented by the dashed line extending parallel to the yield axis, a 50% molar yield of HMF is produced through conversion of fructose in the feedstock (as indicated by the intersection of the dashed line with the HMF yield line). Also, at time "t", the concentration of fructose is significantly reduced (to about 30 to about 35% of the starting concentration). Further, at time "t" in this example, intermediates formation has effectively peaked. As to the formation of off-path product, including humins, applicants have discovered that at a partial conversion of fructose to HMF characterized by a relatively low specified yield of HMF (for example, as shown in FIG. 1 where the yield of HMF is about 50% or less at time "t"), the reaction to these undesired products is significantly reduced, as illustrated by the mass balance being >90%. Generally, off-path product at the partial conversion endpoint is maintained at not more than about 10%, more typically not more than about 8%, in various embodiments does not exceed about 5% (as illustrated in FIG. 1), and in various preferred embodiments can be controlled so as not to exceed about 3%. Thus, in one aspect of the invention the sum of unconverted fructose, the yield of HMF from fructose and the yield of intermediates at the partial conversion endpoint should be at least about 90%, in various embodiments at least about 92%, more typically at least about 95% and in various preferred embodiments at least about 97%.

As demonstrated in Example 7, the specified yield of HMF at the partial conversion endpoint can be suitably increased above 50% and still attain the desired benefits of reduced production of off-path intermediates and improved overall process yield of HMF. More particularly, in accordance with the present invention, the conversion of fructose in the reaction zone is controlled such that at the partial conversion endpoint, the yield of HMF from fructose provided to the reaction zone is not more than about 80%, not more than about 75%, not more than about 70%, not more than about 65%, not more than about 60%, not more than about 55% or not more than about 50%. For economic reasons, the yield of HMF in the reaction zone at the partial conversion endpoint is generally not less than about 30% and typically not less than about 40%. Thus, the yield of HMF from fructose provided to the reaction zone at the partial conversion endpoint is generally controlled at from about 30 to about 80%, from about 30 to about 75%, from about 30 to about 70%, from about 30 to about 65%, from about 30 to about 60%, from about 30 to about 55%, from about 30 to about 50%, from about 40 to about 80%, from about 40 to about 75%, from about 40 to about 70%, from about 40 to about 65%, from about 40 to about 60%, from about 40 to about 55%, from about 40 to about 50% or from about 40 to about 45%. On the other hand, the upper end of the HMF yield at the partial conversion endpoint will depend on various factors, including the nature and concentration of the catalyst, water concentration, solvent selection and other factors that can influence the generation of off-path products. Generally, operation within the ranges for HMF yield at the partial conversion endpoint as disclosed herein are consistent with the adequate control of the production of off-path intermediates while maintaining desired overall process yield of HMF.

In accordance with various embodiments of the invention, to effect partial conversion, the reaction zone is generally maintained at a temperature in the range of from about 50° C. to about 250° C., more typically in the range of from about 80° C. to about 180° C. Generally, higher temperatures increase the reaction rate and shorten the residence time necessary to reach the partial conversion endpoint. The reaction constituents within the reaction zone are typically well-mixed to enhance the conversion rate and the zone is typically maintained at a pressure in the range of from about 1 atm to about 15 atm or from about 2 atm to about 10 atm. In various embodiments, the temperature and pressure within the reaction zone are maintained such that the constituents in the reaction zone are largely maintained in the liquid phase. The pressure in the reaction zone can be maintained by supplying an inert gas such as nitrogen.

The time during which the reaction is carried out in the reaction zone prior to the partial conversion endpoint and before quenching the conversion of fructose and removal of materials from the zone is variable depending upon the specific reaction conditions employed (e.g., reaction temperature, the nature and quantity of the catalyst, solvent selection, water concentration in the reaction zone, etc.) and generally can range from about 1 to about 60 minutes. The composition of the reaction mixture with respect to HMF yield from fructose and the concentration of intermediates to HMF from fructose and of unconverted fructose can be monitored using various means known to those skilled in the art to determine and establish the desired partial conversion endpoint in accordance with the present invention. For example, periodic sampling and analysis (e.g., by HPLC) of the reaction zone materials is but one of several ways to determine and establish the partial conversion endpoint. Additionally or alternatively, the composition of the reaction mixture may be monitored using the dehydration reaction mass balance, wherein a decrease in the mass balance is reflective of an increased concentration of off-path reaction products (including humins) and thus a commensurate decrease in the sum of unconverted fructose, the yield of HMF from fructose and the yield of intermediates. The partial endpoint control method can be integrated into a programmed process control scheme based on an algorithm generated using historical analytical data, and can be updated by on-line or off-line analytical data.

Once the desired partial conversion endpoint is attained, the dehydration reaction and conversion of fructose is typically at least partially quenched to avoid significant additional production of any off-path products (e.g., levulinic acid, formic acid, and soluble and insoluble humins). Typically, at least a portion of the combination produced in the reaction zone is withdrawn for subsequent processing and product recovery as described in detail below. In these and other embodiments, the conversion of fructose can be suitably quenched after the partial conversion endpoint is attained by reducing the temperature of the reaction constituents either within the reaction zone or after being withdrawn from the zone using various industrial means known to those skilled in the art. For example, and without limitation, the reaction constituents may be cooled by flash evaporation, contact with a cooling inert gas, mixing with a liquid diluent, passage through an indirect heat exchanger or a combination of these and other techniques. Typically, in such embodiments, the reaction constituents are cooled to a temperature below about 100° C., more typically, below about 60 or 50° C. It should be understood that other means for quenching the conversion of fructose may be employed without departing from the present invention. For example, in embodiments where a heterogeneous catalyst that is retained in the reaction zone (e.g., a fixed bed catalyst) is employed, the conversion of fructose at the partial conversion endpoint can be quenched by withdrawing some or all of the combination produced from the reaction zone.

Figure 2:
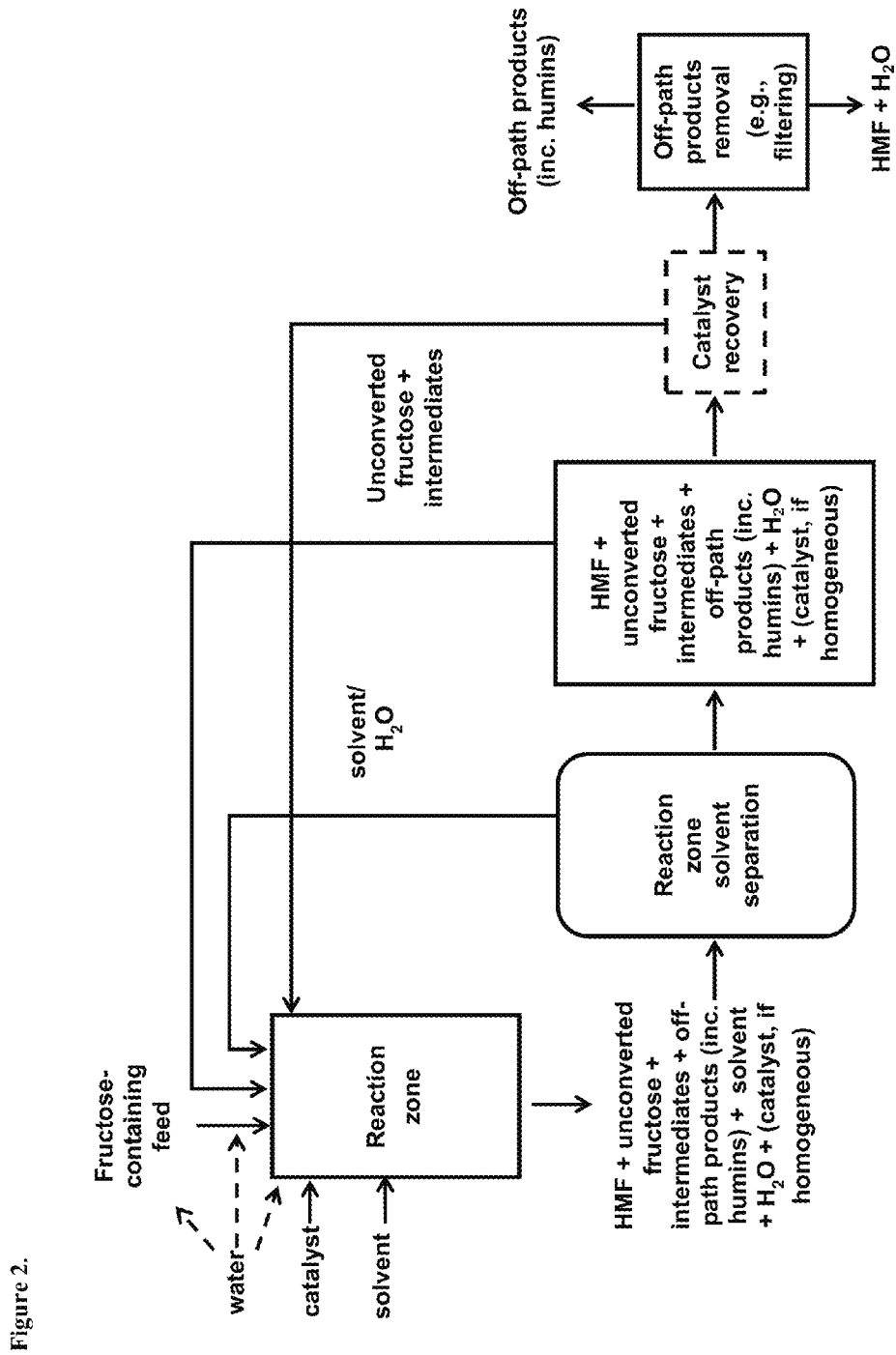
FIG. 2 depicts an example of a process flow diagram illustrating certain aspects of the present invention associated with the partial conversion of the fructose-containing feedstock to HMF, including separate solvent and unconverted fructose separation steps, recovery of catalyst (when applicable) and recycling of some or all of these constituents to the reaction zone or elsewhere.

FIG. 2 illustrates basic process steps employed for the partial conversion of fructose-containing feedstocks to HMF in accordance with the present invention. As illustrated in FIG. 2, feedstock is added as an aqueous solution to the reaction zone, or feedstock and water may be added separately. Additionally, catalyst (heterogeneous or homogeneous) is added to the reaction zone. In the case of a heterogeneous catalyst, the catalyst is typically added to the reaction zone prior to the addition of the feedstock, water and solvent. In the case of a homogeneous catalyst, the catalyst may be pre-mixed with the feedstock and/or solvent before being supplied to the reaction zone (see FIG. 3 et seq.) or may be added before, simultaneously with or after the feedstock, water and/or solvent is added to the reaction zone. Further, solvent may be added to the reaction zone before, simultaneously with or after addition to the reaction zone of one or more of the other reaction zone constituents. Again, in various embodiments of the present invention, regardless of the order in which the constituents are provided to the reaction zone, some or all of the reaction constituents may be mixed prior to addition to the reaction zone or mixed in the reaction zone, all so as to enhance the conversion rate in the reaction zone. Mixing can be undertaken by any of a variety of means well known in the art.

In accordance with the present invention, the conversion step can be carried out in one or more reaction zones. For illustrative purposes, the figures depict only one reaction zone. The process may be carried out in batch, semi-continuously or substantially continuous manner. Any of a variety of well known reactor designs defining at least one reaction zone is suitable for carrying out the process of the present invention. For example, and without limitation, useful reactors include tank reactors, continuously stirred tank reactors (CSTRs), flow through continuous reactors, fixed bed continuous reactors, slurry type reactors and loop reactors, among others. Single reactors may be employed or combinations of several reactors. Again, reactors may comprise one or more reaction zones. Multiple reaction zones in series may be employed using, for example, cascading tank reactors or continuous reactors, or one continuous reactor provided with multiple, separated reaction zones. Those of ordinary skill in the art will appreciate the multitude of reactor configurations which may be employed to achieve the objectives of the present invention.

The output from the reaction zone is a combination comprising HMF, unconverted fructose, intermediates produced during the conversion step, solvent, water and off-path products which may result from the conversion step. Additionally, when homogeneous catalyst is employed, the output from the reactor will include catalyst. Output from the reactor (i.e., the combination removed from the reaction zone at the partial conversion endpoint) includes, quantitatively, at least some amount of each constituent provided to the reaction zone (excluding catalyst, other than impurity amounts, in embodiments in which fixed bed heterogeneous catalysts are employed). For example, in an embodiment employing a tank reactor, the entire contents of the reactor (again, the combination) may be removed after the partial conversion endpoint is attained. Alternatively, for example, in embodiments employing continuous flow reactors, only a portion of the contents in the reaction zone (again, the combination) may be removed in a given period of time to establish a minimum reactor residence time necessary to attain a target partial conversion endpoint.

Figure 3:
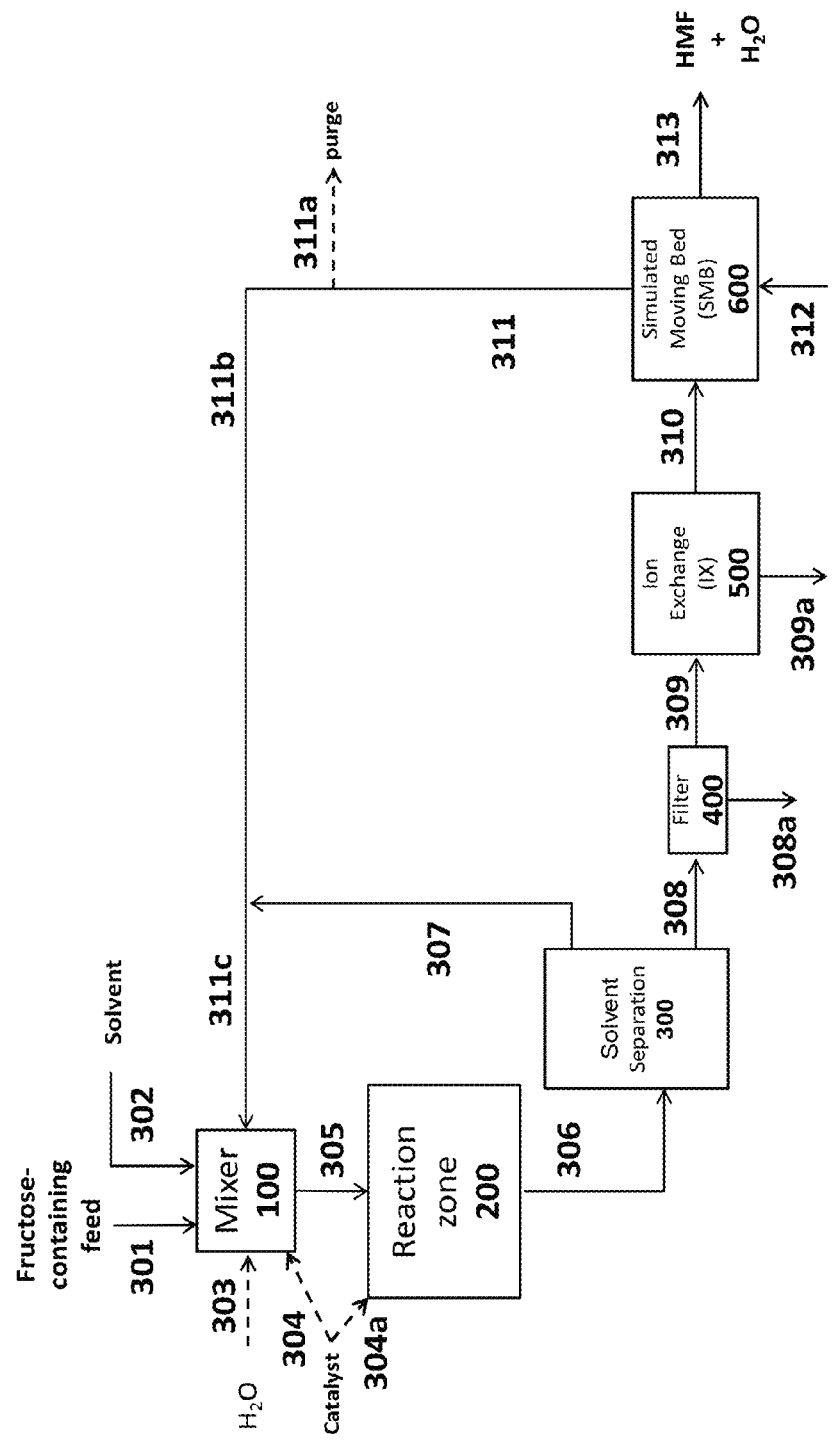
FIG. 3 depicts an example of a process flow diagram of a process employing chromatographic separations technology (e.g., simulated moving bed technology) to effect separation of unconverted fructose and intermediates from the product comprised of HMF and water.

FIG. 3 illustrates an embodiment of the partial conversion process of the present invention using a homogeneous catalyst and employing a combination of a solvent separator 300, a catalyst recovery unit 500, and a product recovery unit 600 to separate and remove unconverted fructose and intermediates from the desired product, HMF in water, and enable recycling of certain reaction constituents. In this embodiment, an aqueous stream of fructose-containing feedstock is supplied via 301 to mixer 100 for mixing reaction constituents (e.g., a stirred tank). Also provided to mixer 100 via 302 is fresh and make up solvent, water via 303, and catalyst via 304. In this embodiment, catalyst may also be provided to a reaction zone 200 via 304a. As contemplated in FIG. 3, supply of catalyst to mixer 100 and reaction zone 200 need not be exclusive to either; instead, it may be supplied to both. The mixed reaction constituents are supplied to the reaction zone via 305. In the reaction zone 200, fructose is converted to HMF until the partial conversion endpoint is attained and then the conversion reaction is suitably quenched as described above. At least a portion of the reaction constituents, product (HMF and water), intermediates to HMF, solvent (in this embodiment the solvent is preferably polar) and off-path products (such as levulinic acid, formic acid, and soluble and insoluble humins, among others) are removed from the reaction zone as a combination and supplied via 306 to solvent separator 300 for separating at least a portion of solvent from the combination. In embodiments where the boiling point of the solvent is significantly lower than the other components of the combination, a simple evaporative separation may be carried out and the heat of vaporization may optionally be used to cool the reaction components in quenching the conversion of fructose. However, in embodiments where, for example, the boiling point of the solvent is relatively close to (whether above or below) that of other components of the combination, a distillation unit may be utilized wherein a fraction composed substantially of solvent and some water, preferably essentially only solvent, can be withdrawn at an appropriate location along the length of the column. Separated solvent is typically condensed to a liquid phase and preferably, as illustrated for example in FIG. 3, supplied via 307 as a component of the recycled mixture provided to the mixer 100 via 311c. In various embodiments, partial solvent separation is preferred as it may be advantageous in assisting the separation of fructose from the product.

The remaining constituents from the combination withdrawn from reaction zone 200 are delivered via 308 to a filtration unit 400. In filtration unit 400 insoluble, typically solid, humins are removed from the stream 308 and disposed of via 308a. The remaining liquid from filtration unit 400 is delivered via 309 to catalyst recovery unit 500 (e.g., an ion exchange unit) designed, for example when HCl or $H_2SO_4$ is the catalyst, to capture the chloride or sulfate ions on the exchange resin prior to the separation of the unconverted fructose from the product. The "catalyst free" eluent from the catalyst recovery unit 500 is supplied via 310 to product recovery unit 600, which in the illustrated embodiment is a continuous chromatographic separation (e.g., simulated moving bed, liquid chromatography or, for short, SMB) unit in which the typically more difficult separation of the unconverted fructose from the product is carried out. SMB units are well known to those of ordinary skill in the art of separations; for example, SMB units are industrially employed in the separation of similar products such as, for example, glucose from fructose. In operation, water is added to the bed via 312 and the mixture of HMF, unconverted fructose and water flows through the multiple columns of the SMB unit to separate HMF from fructose. Ultimately, not more than about 10%, typically not more than about 5%, or not more than about 2% of the unconverted fructose is unseparated from the HMF. The product is removed via 313 and the unconverted fructose is removed via 311. Optionally, a purge stream 311a is provided to remove some of the collected, unconverted fructose and water for any of variety of purposes including, for example, testing, use in another reaction train, to maintain process water balance or for other purposes. The remainder, stream 311b, can be combined with recovered solvent from stream 307 and resupplied to mixer 100 ultimately as a constituent of recycle stream 311c.

Figure 4:
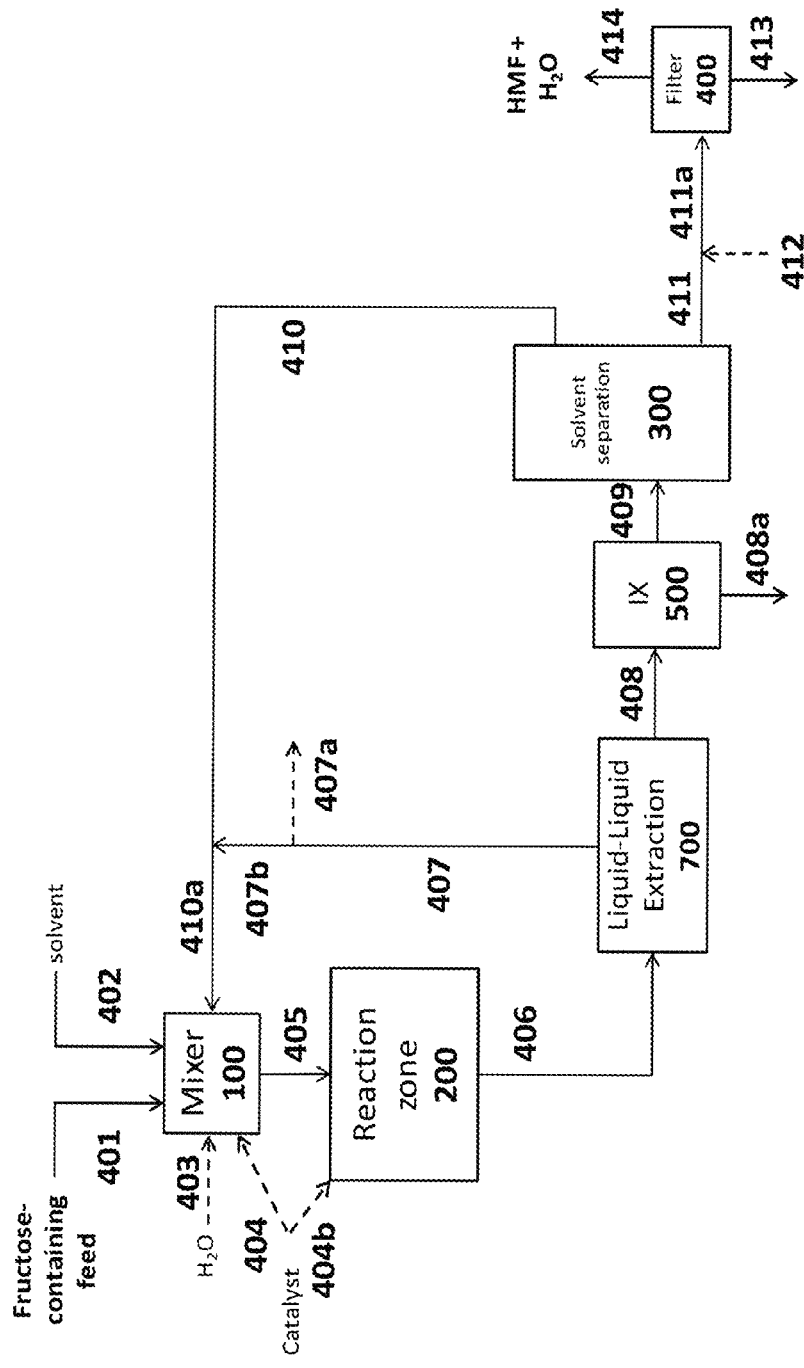
FIG. 4 depicts an example of a process flow diagram of a process wherein a liquid-liquid extraction step is employed to separate initially, and downstream of the reaction zone, at least a portion of the unconverted fructose and intermediates from the combination withdrawn from the reaction zone.

FIG. 4 illustrates an embodiment of the partial conversion process of the present invention using a homogeneous catalyst and employing a combination of a fructose separator 700 for separating unconverted fructose from the combination removed from the reaction zone, for example, by employing liquid-liquid extraction technology, a catalyst recovery unit 500, a solvent separator 300, and a filter 400 for removing off-path products such as insoluble humins from product. In this embodiment, an aqueous stream of fructose-containing feedstock is supplied via 401 to mixer 100 for mixing reaction constituents (e.g., a stirred tank). Also provided to mixer 100 via 402 is fresh and make up solvent, water provided via 403, and catalyst via 404. In this embodiment, catalyst may also be provided to a reaction zone 200 via 404*b*. As contemplated in FIG. 4, supply of catalyst to mixer 100 and reaction zone 200 need not be exclusive to either; instead, it may be supplied to both. The mixed reaction constituents are supplied to the reaction zone via 405. In the reaction zone 200, fructose is converted to HMF until the partial conversion endpoint is attained and then the conversion reaction is suitably quenched as described above. At least a portion of the reaction constituents, product (HMF and water), intermediates to HMF, solvent (in this embodiment the solvent may be polar or non-polar, preferably polar) and off-path products (such as levulinic acid, formic acid, and soluble and insoluble humins, among others) are removed from the reaction zone in combination and supplied via 406 to fructose separator 700 for separating unconverted fructose from the combination removed from the reaction zone.

In one embodiment, fructose separator 700 is a liquid-liquid extraction apparatus. This separation method is well known and encompasses establishing conditions that enable partitioning of one or more constituents into one layer (phase) preferentially as compared to another layer (phase) that forms in the vessel as a result of conditions established therein. Partitioning can be achieved by, for example, choosing an appropriate solvent or by adding to fructose separator 700 a composition of matter that promotes the partitioning. It has been proposed in US 2010/0004437 A1 that unconverted fructose can be extracted from a reaction product comprised of HMF, solvent and water by adding salts such as for example NaCl or $MgCl_2$. In some embodiments, the solvent used to extract unconverted fructose can be used as a cooling medium to quench the conversion of fructose.

An unexpected advantage of embodiments of the present invention in which liquid-liquid separation is employed is that the homogeneous acid catalyst is readily recovered and easily resupplied to the reaction zone with, for example, the unconverted fructose. The partitioned unconverted fructose and at least a portion of the acid catalyst are removed via 407. A part of the partitioned unconverted fructose may optionally be purged via 407*a* for any of a variety of reasons. For example, a portion of the water that may have been partitioned with the unconverted fructose may be separated, for example, by using an evaporator and the unconverted fructose with reduced water content returned to the reaction zone to maintain water balance. Ultimately, not more than about 10%, typically not more than about 5%, or not more than about 2% of the unconverted fructose remains in the liquid fed via 408 to catalyst recovery unit 500.

The remaining constituents partitioned in the other layer (in this embodiment comprising product, catalyst, any partitioning additive and solvent are delivered via 408 to catalyst recovery unit 500 (e.g., an ion exchange unit) designed, for example when HCl or $H_2SO_4$ is the catalyst, the capture the residual chloride or sulfate ions on the exchange resin prior to isolation of the product. In this embodiment it is anticipated that at least a portion, more preferably essentially all, of the homogeneous catalyst is separated during the liquid-liquid extraction process. The catalyst is separated into the phase containing the unconverted fructose and consequently may be recovered and recycled to the reaction zone. The "catalyst free" eluent from the ion exchange unit 500 is supplied via 409 to the solvent separator 300 for separating solvent(s) from the remaining constituents of the combination. In embodiments where the boiling point of the solvent is significantly lower than the other components of the combination, a simple evaporative separation may be carried out; however, in embodiments where, for example, the boiling point of the solvent is relatively close to (whether above or below) that of other components of the combination, a distillation unit may be utilized wherein a fraction composed substantially of solvent and some water, preferably essentially only solvent, can be withdrawn at an appropriate location along the length of the column. Separated solvent is preferably, as illustrated in FIG. 4, supplied via 410 as a component of the recycled mixture provided to the mixer 100 via 410*a*. The remaining constituents from the combination withdrawn from the solvent separator 300 via means 411 are delivered via 411*a*, optionally with additional water supplied via 412, to filter 400. In filter 400 insoluble, typically solid, humins are removed from the stream 411*a* and disposed of via 413. The product is removed from the filter 400 via 414. The unconverted fructose stream 407*b* (and catalyst recovered from the liquid-liquid separation) is mixed with recovered solvent from stream 410 to form stream 410*a* which is resupplied to the mixer 100.

Figure 5:
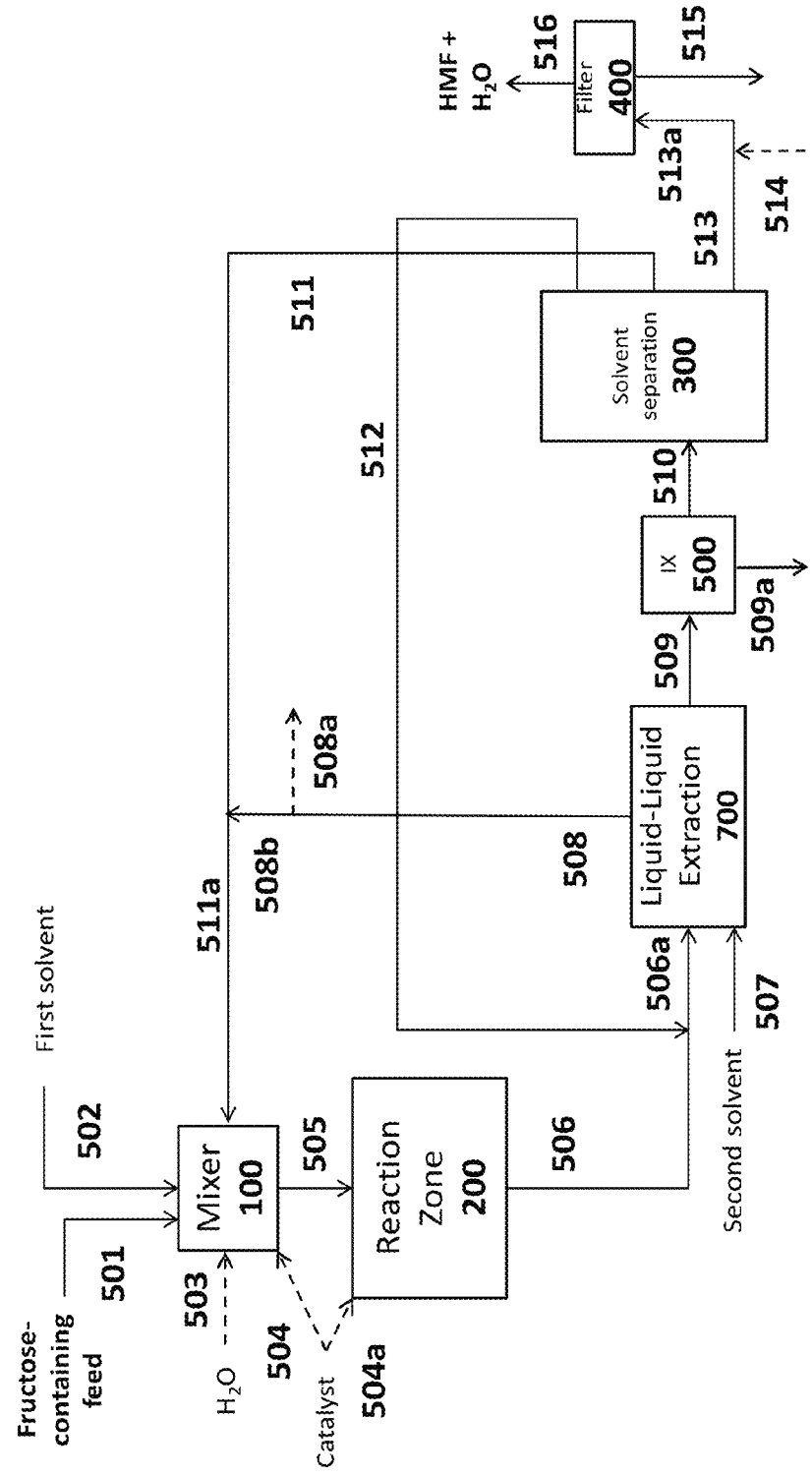
FIG. 5 depicts an example of a process flow diagram of a process wherein a liquid-liquid extraction step is employed to separate initially, and downstream of the reaction zone, at least a portion of the unconverted fructose and intermediates and wherein a second solvent is added downstream of the reaction zone to effect improved partitioning of HMF from unconverted fructose.

FIG. 5 illustrates a preferred embodiment of the partial conversion process of the present invention using an homogeneous catalyst and employing two solvents, one of which is employed to provide enhanced partitioning in fructose separator 700 for separating unconverted fructose from the combination removed from the reaction zone, for example, by employing liquid-liquid extraction technology. The configuration of major aspects of the process illustrated in FIG. 5 is the same as illustrated in FIG. 4. In this embodiment, an aqueous stream of fructose-containing feedstock is supplied via 501 to mixer 100 for mixing reaction constituents (e.g., a stirred tank). Also provided to mixer 100 via 502 is fresh and make up solvent, water provided via 503, and catalyst via 504. In this embodiment, catalyst may also be provided to a reaction zone 200 via 504*a*. Supply of catalyst to mixer 100 and reaction zone 200 need not be exclusive to either; instead, it may be supplied to both. The mixed reaction constituents are supplied to the reaction zone via 505. In the reaction zone 200, fructose is converted to HMF until the partial conversion endpoint is attained and then the conversion reaction is suitably quenched as described above. At least a portion of the reaction constituents, product (HMF and water), intermediates to HMF, solvent (in this embodiment the solvent may be polar or non-polar, preferably polar) and off-path products (such as levulinic acid, formic acid, and soluble and insoluble humins, among others) are removed from the reaction zone in combination and supplied via 506 to fructose separator 700 for separating unconverted fructose from the combination.

In one embodiment, fructose separator 700 is a liquid-liquid extraction apparatus. In this embodiment, a second solvent is added via 507 to the extractor 700. It is known to those skilled in the art that addition of a second solvent will affect the partition coefficient of the soluble components. The partitioned unconverted fructose and separated catalyst is removed via 508 and recycled to the mixer 100 as described in more detail hereinafter. A part of the partitioned unconverted fructose may optionally be purged via 508*a* as described above with respect to FIG. 4. Ultimately, not more than about 10%, typically not more than about 5%, or not more than about 2% of the unconverted fructose is contained in the liquid fed via 509 to catalyst recovery unit 500.

The remaining constituents partitioned into the layer that is the stream 509 (comprising product, catalyst, most or all of both solvents and off-path products) are delivered to catalyst recovery unit 500 (e.g., an ion exchange unit) designed, for example when HCl or $H_2SO_4$ is the catalyst, to capture the residual chloride or sulfate ions on the exchange resin prior to further processing steps. The "catalyst free" eluent from the ion exchange unit 500 is supplied via 510 to the solvent separator 300 for separating the solvents from the remaining constituents of the combination. In this embodiment, a distillation unit is utilized wherein fractions composed substantially of the first solvent and some water, preferably essentially only the first solvent, a fraction composed substantially of the second solvent and some water, preferably essentially only the second solvent, and a bottoms fraction comprised of product and off-path product can be withdrawn at appropriate, different locations along the length of the column. As illustrated in FIG. 5, separated first solvent is supplied via 511 as a component of the recycled mixture provided to the mixer 100 via 511*a*. Separated second solvent is recovered via 512 and supplied to the fructose separator 700 for, for example, a component of stream 506*a* (as shown) or directly to fructose separator 700 (not illustrated). The remaining product and off-path products withdrawn from solvent separator 300 via 513 are delivered via 513*a*, optionally with additional water supplied via 514, to filter 400. In filter 400 insoluble humins and other off-path products are removed from the stream 513*a* and disposed of via 515. The product is removed from the filter 400 via 516. The unconverted fructose stream 508*b* (and recovered catalyst) is then mixed with recovered first solvent stream 511 to form stream 511*a* which is resupplied to the mixer 100.

Figure 6:
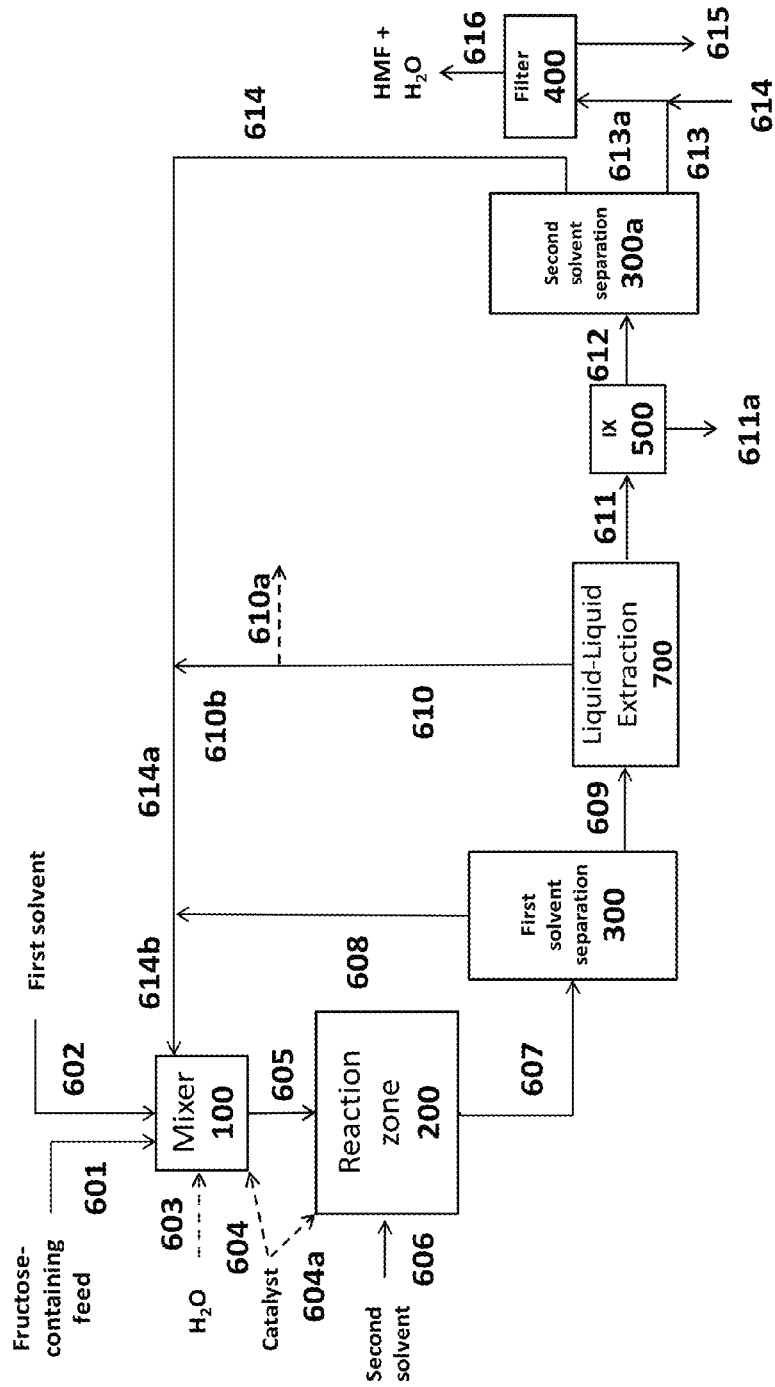
FIG. 6 depicts an example of a process flow diagram of an alternative process configuration employing a liquid-liquid extraction step wherein a polar solvent and non-polar solvent are added to the reaction zone and the polar solvent is removed prior to a liquid-liquid extraction step to enable partitioning of HMF from unconverted fructose.

FIG. 6 illustrates an embodiment of the partial conversion process of the present invention using a homogeneous catalyst and employing two solvents, wherein both solvents are supplied to the reaction zone. In this embodiment, the configuration of major aspects of the process is different from that which is illustrated in FIG. 5 in that two solvent separators 300 and 300*a* are provided wherein one solvent separator 300 is provided upstream of fructose separator 700 to separate the first solvent from the combination removed from the reaction zone via 607 and another solvent separator 300*a* (which may be the same, similar to or different from solvent separator 300) provided downstream of fructose separator 700. In this embodiment, an aqueous stream of fructose-containing feedstock is supplied via 601 to mixer 100 for mixing reaction constituents (e.g., a stirred tank). Also provided to mixer 100 via 602 is fresh and make up first solvent, water provided via 603, and catalyst via 604. In this embodiment, catalyst may also be provided to a reaction zone 200 via 604*a*. Fresh and make-up second solvent is supplied to the reaction zone via 606. Although not illustrated, it will be apparent to those skilled in the art that the second solvent could be provided to the mixer 100. Supply of catalyst to mixer 100 and reaction zone 200 need not be exclusive to either; instead, it may be supplied to both. The mixed reaction constituents are supplied to the reaction zone via 605. In the reaction zone 200, fructose is converted to HMF until the partial conversion endpoint is attained and then the conversion reaction is suitably quenched as described above. At least a portion of the reaction constituents, product (HMF and water), intermediates to HMF, solvent (in this embodiment the solvent may be polar or non-polar, preferably polar) and off-path products (such as levulinic acid, formic acid, and soluble and insoluble humins, among others) are removed from the reaction zone in combination and supplied via 607 to solvent separator 300 for separating at least a portion of the first solvent from the combination removed from the reaction zone. The separated first solvent is removed via 608 to be resupplied to the mixer 100 as a component of stream 614*b*. The remainder from the solvent separator 300 is removed via 609 and supplied to fructose separator 700 for separating unconverted fructose from the combination removed from the reaction zone.

In one embodiment, fructose separator 700 is a liquid-liquid extraction apparatus. In this embodiment, the partitioned unconverted fructose (and catalyst) is removed via 610 and recycled to the mixer 100 as described in more detail hereinafter. Optionally, a purge may be affected via 610*a* to remove a portion of the unconverted fructose for any of a variety of reasons. Also, for example, means may be provided (not illustrated) to remove, for example, by another separation means (such as for example evaporation), a portion of the water that may have been partitioned with the unconverted fructose. Ultimately, not more than about 10%, typically not more than about 5%, or not more than about 2% of the unconverted fructose is contained in the liquid fed via 611 to catalyst recovery unit 500.

The remaining constituents partitioned into the layer that is stream 611 (in this embodiment product, residual catalyst, the second solvent and off-path products) are delivered to catalyst recovery unit 500 (e.g., an ion exchange unit) designed, for example when HCl or $H_2SO_4$ is the catalyst, to capture the residual chloride or sulfate ions on the exchange resin prior to further processing steps. The "catalyst free" eluent from the ion exchange unit 500 is supplied via 612 to solvent separator 300*a* for separating the second solvent from the remaining constituents of the combination. In this embodiment, a distillation or evaporation unit may be utilized depending upon the boiling point of the second solvent relative to that of the product wherein a fraction composed substantially of the second solvent and some water, preferably essentially only the second solvent, is removed via 614 and recycled to mixer 100 as a component of the constituents supplied via 614*a* and 614*b* to the mixer 100. The remaining product and off-path products withdrawn from the solvent separator 300*a* via means 613 are delivered, optionally with additional water supplied via 613*a*, to filter 400. In filter 400 insoluble humins are removed from the filter 400 as a stream 615 which may be disposed. The product is removed from the filter 400 via 616. The unconverted fructose containing stream 610*b* (and separated catalyst) is mixed with recovered second solvent and supplied via 614*a* to mix with recovered first solvent containing stream 608 to form stream 614*b* which is resupplied to mixer 100.

Figure 7:
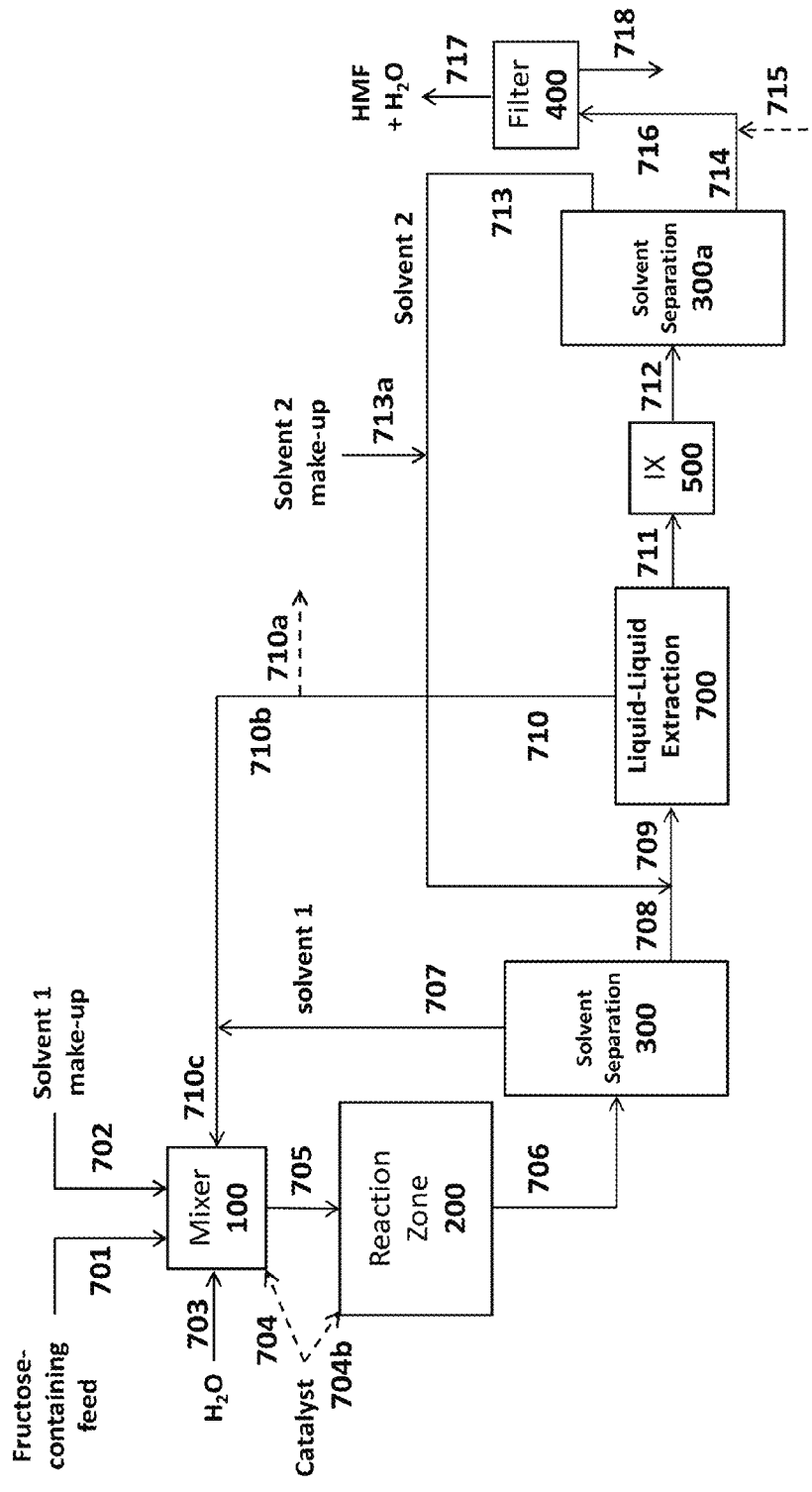
FIG. 7 depicts an example of a process flow diagram of a further alternative process configuration employing two solvents, one of which is employed to provide enhanced partitioning in liquid-liquid extraction to enable portioning of HMF from unconverted fructose.

FIG. 7 illustrates another preferred embodiment of the partial conversion process of the present invention using a homogeneous catalyst and employing two solvents, one of which is employed to provide enhanced partitioning in fructose separator 700 for separating unconverted fructose, catalyst and intermediates from the product. In this embodiment, an aqueous stream of fructose-containing feedstock is supplied via 701 to mixer 100 for mixing reaction constituents (e.g., a stirred tank). Also provided to mixer 100 via 702 is fresh and make up first solvent. Water is provided via 703 and catalyst is supplied via 704 and/or 704*b*. The mixed reaction constituents are supplied to the reaction zone via 705. In the reaction zone 200, fructose is converted to HMF until the partial conversion endpoint is attained and then the conversion reaction is suitably quenched as described above. At least a portion of the reaction constituents, product (HMF and water), intermediates to HMF, solvent (in this embodiment the solvent may be polar or non-polar, preferably polar) and off-path products (such as levulinic acid, formic acid, and soluble and insoluble humins, among others) are removed from the reaction zone in combination and supplied via 706 to solvent separator 300 for separating at least a portion (preferably, substantially all) of the first solvent from the reaction combination. The solvent separation technique employed may be selected from among many options known to those skilled in the art (e.g., flash evaporation). The first solvent is removed as stream 707 for resupply to mixer 100 as a component of stream 710*c*.

The remaining constituents are removed from the first solvent separator 300 as stream 708. A second solvent, which is different from the first solvent, is added to stream 708 via 713. For example, in this embodiment, the first solvent can be an ether, such as DME and the second solvent can be a ketone, such as MIBK. The resulting stream 709 is supplied to fructose separator 700. Fructose separator 700 is a liquid-liquid extraction apparatus and separates a liquid phase comprising unconverted fructose, intermediates and catalyst from the composition of the stream 709. The partitioned liquid phase comprising unconverted fructose, intermediates and separated catalyst is removed via 710 and recycled to mixer 100 as described in more detail hereinafter. Optionally, a part of the liquid for any of a variety of reasons may be purged via 710*a*. For example, means may be provided (not illustrated) to remove, for example, by another separation means (such as for example evaporation), a portion of the water that may have been partitioned with the unconverted fructose.

The remaining constituents partitioned into the layer that is the stream 711 (comprising product, some catalyst, preferably substantially all of the second solvent and off-path products) are delivered to catalyst recovery unit 500 (e.g., an ion exchange unit) designed, for example when HCl or $H_2SO_4$ is the catalyst, to capture the residual chloride or sulfate ions on the exchange resin prior to further processing to recover product. Ultimately, not more than about 10%, typically not more than about 5%, or not more than about 2% of the unconverted fructose is contained in the liquid fed via 711 to the ion exchange unit 500. Upon effecting ion exchange to capture substantially all of the remaining catalyst, the "catalyst free" eluent from the ion exchange unit 500 is supplied via 712 to a second solvent separator 300*a* for separating the second solvent from the product. In this embodiment, a flash evaporation unit may be utilized to vaporize the second solvent and some water, preferably essentially only the second solvent. The bottoms fraction, now comprised of product and off-path materials can be withdrawn via 714. As illustrated in FIG. 7, separated first solvent from solvent separator 300 is supplied via 710*b* as a component of the recycled mixture provided to mixer 100 via 710*c*. Separated second solvent from second solvent separator 300*a* is recovered via 713 and resupplied to the fructose separator 700. Make-up second solvent, if needed, may be added via 713*a*. The remaining product and off-path materials withdrawn from second solvent separator 300*a* via 714 are delivered via 716, optionally with additional water supplied via 715, to filter 400. In filter 400 insoluble humins and other off-path materials are removed and disposed of via 718. The product is then removed from the filtration unit 400 as stream 717. The unconverted fructose containing stream 710*b* (and separated catalyst) is then mixed with recovered first solvent stream 707 to form stream 710*c* which is resupplied to mixer 100.

In another aspect of the invention, selective membrane separation techniques (e.g., ultra-filtration and/or nano-filtration) are employed to separate unconverted fructose, intermediates and HMF from the other constituents of the combination withdrawn from the reaction zone. Selective membrane separation techniques utilized to treat the aqueous combination withdrawn from the reaction zone as disclosed herein provide effective recovery of unconverted fructose and intermediates for recycle, increased overall process yields and a high degree of product recovery.

Figure 8:
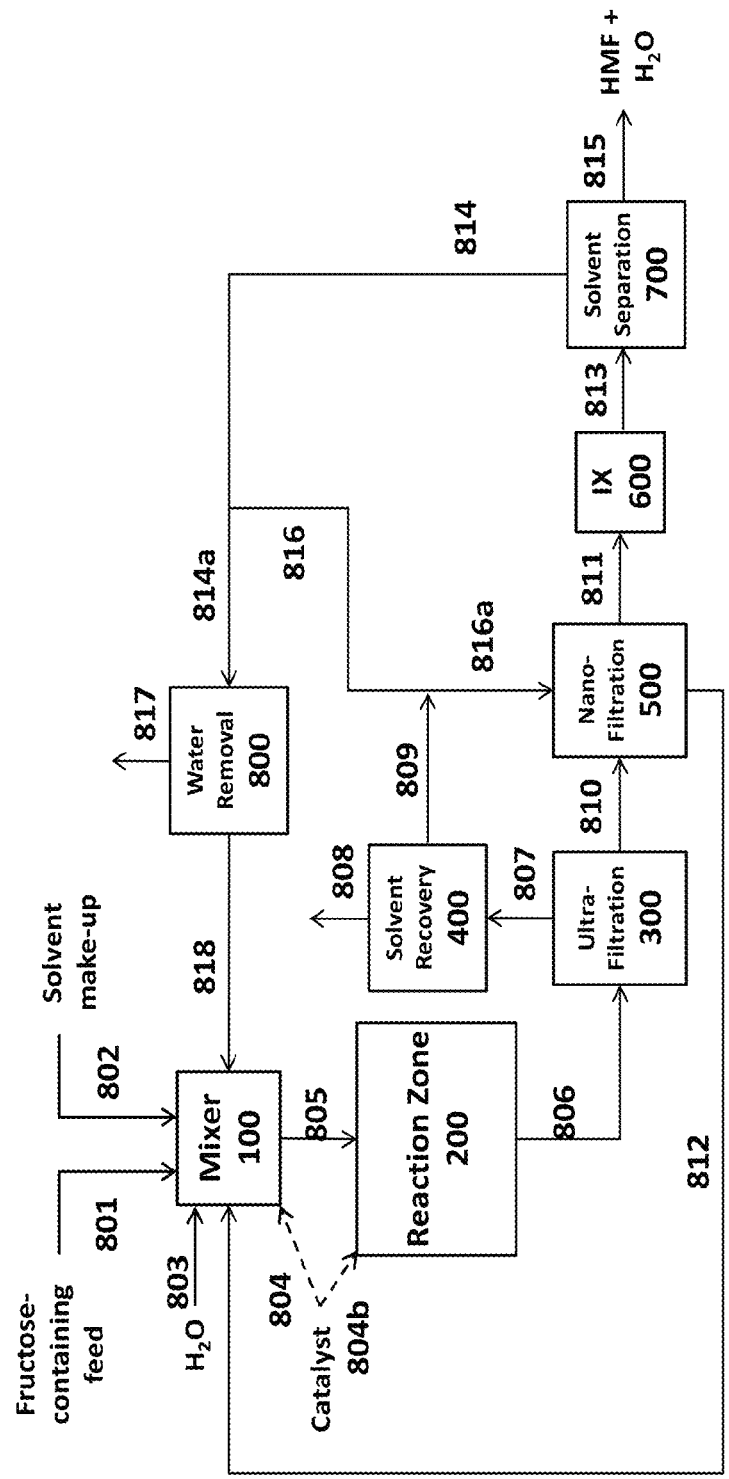
FIG. 8 depicts an example of a process flow diagram of a process configuration employing the use of ultra-filtration and nano-filtration to enable the separation of HMF from unconverted fructose and intermediates.

FIG. 8 illustrates another embodiment of the partial conversion process of the present invention using a homogeneous catalyst and an employing ultra-filtration unit 300 for the removal of humins, and a nano-filtration unit 500 for the separation of unconverted fructose and intermediates from the desired HMF product to enable the recycling of certain reaction constituents back to the reaction zone 200.

An aqueous stream of fructose-containing feedstock is supplied via 801 to mixer 100 for mixing reaction constituents (e.g., a stirred tank). Also provided to mixer 100 via 802 is fresh and make up solvent. Water is optionally provided via 803 and catalyst is supplied via 804 and/or 804*b*. The mixed reaction constituents are supplied to the reaction zone 200 via 805. In the reaction zone 200, fructose and reaction intermediates are converted to HMF until the partial conversion endpoint is attained and then the conversion reaction is suitably quenched as described above. At least a portion of the reaction constituents, product (HMF and water), intermediates to HMF, solvent (in this embodiment the solvent may be polar or non-polar, preferably polar) and off-path products (such as levulinic acid, formic acid, and soluble and insoluble humins, among others) are removed from the reaction zone in combination via 806 and subjected to selective membrane separation treatment as described in detail below.

The aqueous combination removed from the reaction zone intended for selective membrane separation treatment may be collected in an optional feed tank (not shown). In order to prevent fouling and the resulting loss of flux and extend the useful life of the selective membrane(s) employed in membrane separation unit(s), the suspended solids content in the aqueous combination removed from the reaction zone is optionally controlled. Typically, the aqueous combination will contain less than about 10,000 ppm of suspended solids. To enhance membrane performance and extend membrane life, the suspended solids content of the aqueous combination subjected to membrane separation may be reduced to less than about 1000 ppm, less than about 500 ppm, or less than about 100 ppm. The solids content of the aqueous combination removed from the reaction zone in 806 can be reduced, as necessary, to the desired level in an optional solids reduction stage (not shown). The solids reduction stage may represent a point of dilution wherein the aqueous combination is diluted with a quantity of an aqueous diluent (e.g., process water). Alternatively, the solids content of the aqueous combination can be reduced by a conventional filtration operation. The filtration operation can be suitably conducted in a batch mode (e.g., using bag filters) or in a continuous mode allowing for continuous flow of the aqueous combination through the solids reduction stage. Suitable continuous filters include cross-flow filters and continuous back-pulse filters wherein a portion of the filtrate is used to periodically back-pulse the filter media to dislodge and remove separated solids. Typically, the filter media employed is capable of separating and removing suspended solids greater than about 250 μm in size from the aqueous combination. It should be understood that any optional solids reduction stage may comprise a combination of dilution, filtration and/or other operations to attain the desired solids content in the aqueous combination prior to selective membrane separation treatment. The suspended solids content of the aqueous combination removed from the reaction zone can be readily determined by analytical methods known in the art such as by turbidity measurement (e.g., nephelometric turbidity units or NTU) and correlation of the turbidity reading to a known standard or by other methods known to those skilled in the art.

Following optional suspended solids reduction, the aqueous reaction combination withdrawn from the reaction zone is supplied via 806 to ultra-filtration unit 300 in which the aqueous reaction combination is contacted with one or more ultra-filtration membranes to produce a concentrate or retentate stream 807 containing at least a portion (preferably, substantially all) of the humins from the reaction combination and a permeate stream 810 containing unconverted fructose, intermediates, catalyst and HMF and depleted in humins relative to the aqueous reaction combination. Stream 807 is then fed to a solvent recovery unit 400 for the recovery of solvent from the humins-containing retentate stream. The humins are isolated via stream 808 and the recovered solvent stream 809 may be combined with stream 816 and supplied as diluents stream 816a to the downstream nano-filtration unit 500 as described below.

The ultra-filtration permeate stream 810 in combination with diluent stream 816a is supplied to nano-filtration unit 500 and contacted with one or more nano-filtration membranes to produce a permeate stream 811 containing HMF product, solvent and water and a retentate stream 812 containing at least a portion (preferably, substantially all) of the unconverted fructose and intermediates. Nano-filtration retentate stream 812 may also contain some portion of HMF and catalyst (i.e., homogeneous catalyst, if present) that did not permeate the nano-filtration unit 500. Nano-filtration permeate stream 811 may also contain catalyst, and some residual amounts of humins, fructose and reaction intermediates that have passed through the ultra-filtration and nano-filtration units. Stream 812 is supplied to mixer 100 for recycle to reaction zone 200.

The ultra-filtration unit 300 and nano-filtration unit 500 may comprise one or more ultra-filtration or nano-filtration membranes or modules and may be configured as either a single pass or multi-pass system, typically in a cross-flow arrangement wherein the feed flow is generally tangential across the surface of the membrane. The membrane modules may be of various geometries and include flat (plate), tubular, capillary or spiral-wound membrane elements and the membranes may be of mono- or multilayer construction. In some embodiments, tubular membrane modules may allow for higher solids content in the mother liquor solution to be treated such that solids reduction upstream of the membrane separation unit is not required or can be significantly reduced. The separation membranes and other components (e.g., support structure) of the membrane modules are preferably constructed to adequately withstand the conditions prevailing in the feed mixture and the membrane separation unit. For example, the separation membranes are typically constructed of organic polymers such as cross-linked aromatic polyamides in the form of one or more thin film composites. Specific examples of suitable ultra-filtration membranes include, for example and without limitation, spiral wound GE UF membranes having a molecular weight cut-off (MWCO) of 1000 available from GE Water & Process Technologies, Inc. (Trevose, Pa.), a division of GE Power & Water. Specific examples of suitable nano-filtration membranes include, for example and without limitation, spiral wound Dairy NF membranes having a MWCO of 150 and spiral wound H series membranes having a MWCO of 150-300 available from GE Water & Process Technologies, Inc.

Selective membrane separation techniques such as ultra-filtration and nano-filtration are pressure-driven separation processes driven by the difference between the operating pressure and the osmotic pressure of the solution on the feed or retentate side of a membrane. The operating pressure within a membrane separation unit will vary depending upon the type of membrane employed, as osmotic pressure is dependent upon the level of transmission of solutes through the membrane. Operating pressures in the membrane separation unit are suitably achieved by passing the feed stream (e.g., incoming reaction constituents in the combination removed from the reaction zone) through one or more pumps upstream of the membrane unit, for example, a combination booster pump and high-pressure pump arrangement. Generally, ultra-filtration operations exhibit lower osmotic pressures than nano-filtration operations, given the same feed solution. The driving force for transmission through the membrane (i.e., permeate flux) increases with the operating pressure. However, the benefits of increased operating pressure must be weighed against the increased energy (i.e., pumping) requirements and the detrimental effects (i.e., compaction) on membrane life.

Typically, the operating pressure utilized in the ultra-filtration operation is less than about 800 kPa absolute and preferably from about 200 to about 500 kPa absolute. Typically, the operating pressure utilized in the nano-filtration operation is less than about 1200 kPa absolute and preferably from about 600 to about 900 kPa absolute. High temperatures tend to decrease the useful life of selective membranes. Accordingly, the temperature of the aqueous combination introduced into the ultra-filtration membrane separation unit 300 is generally from about 20° C. to about 100° C., and typically from about 30° C. to about 60° C. or from about 30° C. to about 50° C. If necessary, the aqueous combination can be cooled prior to being introduced into membrane separation unit 300 by methods conventionally known in the art including, for example, indirect heat exchange with other process streams or with cooling water (e.g., as part of the quench step).

In order to maintain or enhance membrane separation efficiency and permeate flux, the membranes should be periodically cleaned so as to remove contaminants from the surface of the membrane. Suitable cleaning includes cleaning-in-place (CIP) operations wherein the surface of the membrane is exposed to a cleaning solution while installed within ultra-filtration unit 300 and nano-filtration unit 500. Some systems monitor the conductivity of the permeate, as conductivity can be correlated to the concentration of components that pass through the membrane. An increase in conductivity in the permeate may indicate an increase in transmission of the desired retentate compounds through the membrane and can be used to signal the need for cleaning operations. Additionally, a fall in permeate flow with all other factors remaining constant may indicate fouling and the need for cleaning operations. Cleaning protocols and cleaning solutions will vary depending on the type of separation membrane employed and are generally available from the membrane manufacturer. In order to not damage the membranes and unnecessarily shorten membrane life, the CIP operation is preferably conducted using a solution of a standard pH at pressure and temperature conditions known to those skilled in the art. In some applications, it may be advantageous to conduct a cleaning operation on new separation membranes prior to use in the membrane separation operation in order to improve membrane performance.

The nano-filtration permeate stream 811 is delivered to an optional catalyst recovery unit 600. For example, catalyst recovery unit 600 may comprise an ion exchange unit designed, for example when HCl or $H_2SO_4$ is the catalyst, to capture the residual chloride or sulfate ions on the exchange resin prior to further processing to recover the HMF product. Ultimately, not more than about 10%, and typically not more than about 5%, or not more than about 1% of the unconverted fructose and reaction intermediates are contained in the liquid fed via 811 to the ion exchange unit 600. Upon effecting ion exchange to capture substantially all of the remaining catalyst, the "catalyst free" eluent from the ion exchange unit 600 is supplied via 813 to a solvent separator 700 for separating the solvent and a portion of the water from the product. For example, a flash evaporation unit may be utilized to vaporize the solvent and some water, preferably essentially only the solvent. The bottoms fraction, now comprised of primarily HMF and water can be withdrawn via 815.

Separated solvent from solvent separator 700 is recovered in 814. Stream 814 optionally provides diluent for nano-filtration unit 500 via 816. The remainder of the stream is supplied to the water removal unit 800 via 814a. A portion (preferably, substantially all) of the water in stream 814a can be removed as stream 817 employing of a number of methods including, but not limited to, distillation, adsorption, pervaporation and membrane separation. The water-reduced stream 818 containing primarily solvent is supplied to mixer 100 for recycle to reaction zone 200.

The process described by FIG. 8 contains solvent separator unit 700 which can be used to remove solvent and produce stream 815 containing HMF and water. In an alternative embodiment, unit 700 may configured to remove water via stream 814 (either as a pure water stream or as an azeotrope with the solvent) producing stream 815 containing HMF and solvent, which may optionally contain some water.

While the various process schemes illustrated in the accompanying Figures provide for a product containing HMF as an aqueous solution, it will be evident to one of skill in the art that any of the process schemes may be readily adapted to produce HMF dissolved in a solvent other than water, or HMF dissolved in a solvent/water combination.

EXAMPLES

The following non-limiting examples are provided to further illustrate the present invention.

Example 1

Fructose, water, HCl, NaCl and organic solvent were combined in a sealed reactor in the proportions detailed in Table 1. The reactor was heated with stirring to the temperature and for the time reported in Table 1. On cooling, samples of all layers were taken and the products were analyzed and composition determined by HPLC. HPLC analysis in Examples 1 through 6 was conducted on an Agilent 1200 LC system using a Thermo Scientific Hypercarb, 3.0×30 mm, 5 um column (guard) and an Agilent Zorbax SB-Aq 3.0×100 mm, 3.5 um column (analytical) at 46° C. The species were eluted under isocratic conditions of using a mixture of 90% (v/v) solvent mixture A (0.1% formic acid in water) and 10% (v/v) solvent mixture B (0.1% formic acid in 50:50 methanol:water) at a flow rate of 1.0 mL/min. Fructose, glucose and intermediates were detected using a universal charged aerosol detector (CAD), while HMF was detected by UV at 254 nm. Fructose, glucose and HMF were quantified by fitting to calibration curves generated from pure standards. Intermediates were quantified using a calibration curve generated from a structurally related compound. The distributions of products are described in Table 1.

TABLE 1

| Entry | Fructose wt % | HCl mol % | Water wt % | Solvent | Total Solvent Added (mL) | NaCl (mg) | Run Temp. (° C.) | Run Time (min) | Unconverted Fructose mol % | Intermediates mol % | HMF mol % | Sum of mol % Fructose + Intermediates + HMF |
|---|---|---|---|---|---|---|---|---|---|---|---|---|
| 1 | 20 | 5 | 20 | 2Butanol | 4 | 130 | 120 | 30 | 35 | 16 | 49 | 100 |
| 2 | 20 | 5 | 20 | 2-Butanol | 4 | 0 | 140 | 15 | 29 | 20 | 47 | 96 |
| 3 | 10 | 5 | 15 | Diglyme | 4 | 0 | 100 | 60 | 26 | 26 | 43 | 95 |
| 4 | 10 | 10 | 15 | Diglyme | 4 | 0 | 100 | 30 | 26 | 26 | 43 | 94 |
| 5 | 10 | 20 | 15 | Diglyme | 4 | 0 | 100 | 15 | 30 | 21 | 43 | 94 |
| 6 | 10 | 10 | 20 | Diglyme | 4 | 0 | 100 | 60 | 36 | 20 | 41 | 97 |
| 7 | 10 | 10 | 20 | Diglyme | 4 | 0 | 100 | 60 | 37 | 20 | 42 | 99 |
| 8 | 10 | 15 | 20 | Diglyme | 4 | 0 | 100 | 30 | 33 | 24 | 41 | 99 |
| 9 | 10 | 5 | 20 | Dioxane | 2 | 0 | 130 | 15 | 35 | 19 | 46 | 100 |
| 10 | 10 | 5 | 20 | Dioxane | 2 | 0 | 140 | 15 | 45 | 13 | 41 | 100 |
| 11 | 15 | 10 | 15 | Glyme | 4 | 0 | 110 | 30 | 26 | 23 | 48 | 97 |
| 12 | 20 | 5 | 20 | Glyme | 4 | 0 | 140 | 20 | 30 | 25 | 43 | 98 |
| 13 | 10 | 5 | 20 | Glyme | 2 | 0 | 140 | 15 | 32 | 19 | 48 | 99 |
| 14 | 30 | 1 | 20 | Glyme | 4 | 0 | 160 | 30 | 29 | 23 | 43 | 95 |
| 15 | 10 | 5 | 20 | THF | 2 | 0 | 140 | 30 | 35 | 9 | 44 | 88 |

Example 2

13.0 g of HFCS-90 (77.2% DS, 93.7% fructose, 4.1% glucose, 2.2% DP2+), 3.3 mL of 1 M aq. HCl, 12.6 mL of water, and 80.8 mL of dimethoxyethane (DME) were combined in a sealed container and heated with stirring at 120° C. for 60 minutes. On cooling, a sample was taken and analyzed by HPLC for fructose+glucose, reaction intermediates, and HMF. HMF yield (based on total sugars): 48%; sum of unconverted fructose+mol % yield of intermediates+mol % yield of HMF: 99%.

Example 3

10 g of fructose (56 mmol fructose), 3.3 mL of 1 M aq. HCl (3.3 mmol HCl), 18 mL of water, and 80 mL of dimethoxyethane (DME) were combined in a sealed container and heated with stirring at 150° C. for 65 minutes. The solution was cooled and the DME was removed by vacuum rotary evaporation. To the resulting aq. solution was added 60 mL of methyl isobutyl ketone (MIBK) and the mixture was stirred vigorously and allowed to phase separate. Samples from each layer were taken and analyzed by HPLC for fructose, reaction intermediates, and HMF. HMF yield (based on fructose): 36%; sum of unconverted fructose+mol % yield of intermediates+mol % yield of HMF: 98%. Table 2 reports the distribution of the reaction constituents (fructose, reaction intermediates and HMF) in the different layers (phases).

TABLE 2

| Layer | Volume (mL) | Fructose mol % | Intermediates mol % | HMF mol % |
|---|---|---|---|---|
| Top | 59 | 0% | 0% | 90% |
| Bottom | 9 | 100% | 100% | 10% |

Example 4

120 g of fructose (666 mmol fructose), 33 mL of 1 M aq. HCl (33 mmol HCl), 67 mL of 5 M aq. NaCl (333 mmol NaCl), and 400 mL of 2-BuOH (1$^{st}$ solvent) were combined in a sealed container and heated with stirring at 120° C. for 45 minutes. On cooling to room temperature, 50 mL of hexane (2$^{nd}$ solvent) was added, the mixture was stirred vigorously, and allowed to separate. Samples from each layer were taken and analyzed by HPLC for fructose, reaction intermediates, and HMF. HMF yield (based on fructose): 30%; sum of unconverted fructose+mol % yield of intermediates+mol % yield of HMF: 93%. Table 3 reports the mole fractions of reaction constituent (fructose), intermediates and product in the different layers (phases).

TABLE 3

| Layer | Volume (mL) | Moles fructose | Moles reaction intermediates | Moles HMF |
|---|---|---|---|---|
| Top | 544 | 0.021 | 0.00 | 0.181 |
| Bottom | 170 | 0.259 | 0.141 | 0.022 |

Example 5

To the bottom layer of Example 4 was added 45 g fructose (242 mmol fructose), 29 mL of 1 M aq. HCl (29 mmol HCl), and 400 mL of 2-BuOH. The mixture was heated with stirring in a sealed container at 120° C. for 45 minutes. On cooling to room temperature, 50 mL of hexane was added, the mixture was stirred vigorously, and allowed to separate. Samples from each layer were taken and analyzed by HPLC for fructose, reaction intermediates, and HMF. HMF yield (based on fructose +reaction intermediates): 32%; sum of unconverted fructose+mol % yield of intermediates+mol % yield of HMF: 93%. Table 4 reports the mole fractions of reaction constituent (fructose), intermediates and product in the different layers (phases).

TABLE 4

| Layer | Volume (mL) | Moles fructose | Moles reaction intermediates | Moles HMF |
|---|---|---|---|---|
| Top | 585 | 0.027 | 0.00 | 0.210 |
| Bottom | 159 | 0.230 | 0.139 | 0.021 |

Example 6

In this Example, commercially available acid-functionalized polymeric ion exchange resins were tested for fructose dehydration to HMF using the following catalyst testing protocol.

Catalyst was weighed into a glass vial insert followed by addition of 300-1000 µl of 5 wt % fructose, fructose+glucose and/or Invertose HFCS-90 solution plus solvent (5:1 organic solvent to water). The glass vial insert was loaded into a reactor and the reactor was closed. The atmosphere in the reactor was replaced with nitrogen and pressurized to 300 psig at room temperature. Reactor was heated to 120° C. and maintained at 120° C. for 30-120 minutes while vials were shaken. After the specified reaction time, shaking was stopped and the reactor was rapidly cooled to 40° C. Pressure in the reactor was then slowly released. The solutions were diluted with water and analyzed by liquid chromatography with CAD and UV detection and gas chromatography with flame ionization detection. The particulars of a variety of runs using the catalysts are reported in Table 5. For entries 6, 7 and 9, which utilized solutions comprised of fructose with 10-20% glucose by weight, mol % unconverted fructose reported in Table 5 reflects the amount of fructose+glucose within the reaction solution at time of quench.

TABLE 5

| Entry | Substrate | Resin | H+ (meq/g) | Catalyst (mg) | Reaction Volume (ul) | Solvent | Run Time (min) | Unconverted Fructose mol % | Intermediates mol % | HMF mol % | Sum of unconverted Fructose + Intermediates + HMF |
|---|---|---|---|---|---|---|---|---|---|---|---|
| 1 | Fructose | Amberlyst 15 | 4.85 | 10 | 400 | Glyme | 30 | 34 | 10 | 49 | 94 |
| 2 | Fructose | Amberlyst 15 | 4.85 | 9 | 500 | Glyme | 30 | 40 | 12 | 42 | 95 |
| 3 | Fructose | Amberlyst 15 | 4.85 | 9 | 750 | Glyme | 30 | 49 | 12 | 31 | 92 |
| 4 | Fructose | Purolite 275 DR | 4.26 | 10 | 500 | Glyme | 30 | 36 | 11 | 45 | 92 |
| 5 | Fructose | Purolite 275 DR | 4.26 | 4 | 1000 | Glyme | 120 | 50 | 0 | 45 | 95 |
| 6 | Invertose HFCS-90 | Purolite 275 DR | 4.26 | 7 | 400 | Glyme | 30 | 44 | 11 | 42 | 97 |
| 7 | Fructose + Glucose (4:1) | Purolite 275 DR | 4.26 | 7 | 400 | Glyme | 30 | 45 | 8 | 39 | 92 |

TABLE 5-continued

| Entry | Substrate | Resin | H+ (meq/g) | Catalyst (mg) | Reaction Volume (ul) | Solvent | Run Time (min) | Unconverted Fructose mol % | Intermediates mol % | HMF mol % | Sum of unconverted Fructose + Intermediates + HMF |
|---|---|---|---|---|---|---|---|---|---|---|---|
| 8 | Fructose | Purolite 275 DR | 4.26 | 9 | 750 | Glyme | 30 | 48 | 12 | 34 | 94 |
| 9 | Fructose + Glucose (9:1) | Purolite 275 DR | 4.26 | 6 | 600 | Glyme | 30 | 54 | 12 | 30 | 96 |
| 10 | Fructose | Purolite 275 DR | 4.26 | 7 | 600 | Glyme | 30 | 49 | 13 | 36 | 97 |
| 11 | Fructose | Purolite 275 DR | 4.26 | 4 | 600 | IPA | 120 | 40 | 2 | 49 | 90 |
| 12 | Fructose | Purolite 275 DR | 4.26 | 11 | 400 | IPA | 30 | 41 | 8 | 42 | 91 |
| 13 | Fructose | Purolite 275 DR | 4.26 | 5 | 1000 | IPA | 120 | 52 | 0 | 37 | 90 |

Example 7

In this example, high fructose corn syrup was converted to HMF in a continuous flow reactor.

The flow reactor consisted of a 0.25"×73" zirconium tube having an approximate volume of 30.0 mL. The reactor tube was vertically mounted in an aluminum block heater equipped with PID controller. Feed solutions were delivered in upflow mode using two HPLC pumps and the reactor pressure was controlled at 300 psi by means of a back pressure regulator.

Two feed solutions were prepared, Feed 1: 10 wt % HFCS-90, dissolved in Dioxane/$H_2O$ (4/1 by volume); and Feed 2: 10 wt % HFCS-90, 0.12 wt % HCl dissolved in Dioxane/$H_2O$ (4/1 by volume).

Figure 9:
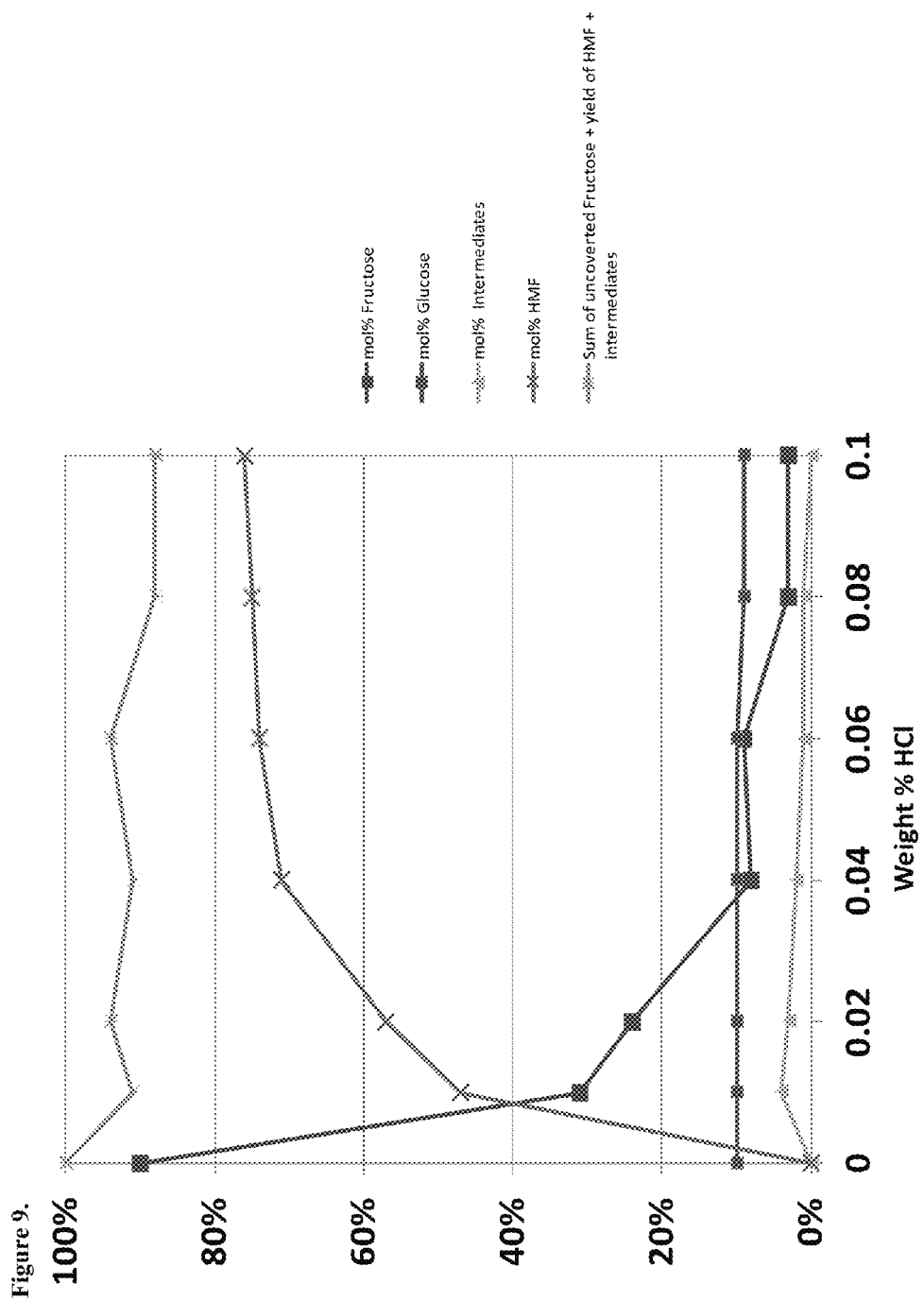
FIG. 9 graphically illustrates the conversion of fructose to HMF in a continuous flow reaction zone as a function of HCl concentration at a fixed residence time, highlighting changes in fructose, HMF and intermediates concentrations.

The reaction was performed at 120° C. with a fixed residence time of 5 minutes and a total feed flow rate of 6 mL/min. Reaction conversion was controlled by varying the amount of HCl through changes in the flow ratio of Feed 1 and Feed 2. Reaction progress was monitored and product composition was determined by HPLC analysis on a Thermo Ultimate 3000 analytical chromatography system using a porous graphitic stationary phase (Hypercarb, 3.0>100 mm, 5 um) at 30° C. Fructose and glucose were eluted under isocratic conditions of 0.005% v/v $NH_4OH$ in $H_2O$ at a flow rate of 0.6 mL/min. Intermediates and 5-(hydroxymethyl)furfural (HMF) were eluted by employing a gradient of up to 60% MeOH at a flow rate of 1.0 mL/min. Fructose, glucose and intermediates were detected using a universal charged aerosol detector (CAD) and HMF was detected by UV at 254 nm. Fructose, glucose, and HMF were quantified by fitting to calibration curves generated from pure standards. Intermediates were quantified using a calibration curve generated from a structurally related reference compound. The results are summarized in the Table 6 below and the data from this example is depicted graphically in FIG. 9.

TABLE 6

| wt % HCl | Unconverted Fructose mol % | Glucose mol % | Intermediates mol % | HMF mol % | Sum of mol fraction % of unconverted Fructose + Intermediates + mol % HMF |
|---|---|---|---|---|---|
| 0.00 | 90% | 10% | 0% | 0% | 100% |
| 0.01 | 31% | 10% | 4% | 47% | 91% |
| 0.02 | 24% | 10% | 3% | 57% | 94% |
| 0.04 | 8% | 10% | 2% | 71% | 91% |
| 0.06 | 9% | 10% | 1% | 74% | 94% |
| 0.08 | 3% | 9% | 1% | 75% | 88% |
| 0.10 | 3% | 9% | 0% | 76% | 88% |

Example 8

In this example, ultra-filtration and nano-filtration membranes were used to remove humins from the aqueous product effluent resulting from conversion of fructose to HMF.

Product effluent for testing of ultra- and nano-filtration was produced under conditions analogous to those described in Example 7, but using 1,2-dimethoxyethane (DME) as the solvent (4/1 DME/water by volume). This partial conversion continuous flow process gave an aqueous product mixture consisting of 24 mol % fructose, 8 mol % glucose, 9 mol % intermediates, 56 mol % HMF and 3 mol % unidentified oligomeric or polymeric materials referred to as humins.

The HCl in the collected product effluent was neutralized with 1 eq of NaOH prior to removal of DME by rotary evaporation. The remaining crude aqueous product mixture was diluted 3.8 times by volume with deionized water and subjected to ultra-filtration and nano-filtration treatment for removal of humins.

In one test, cross-flow ultra-filtration was performed by circulating 2 L of the opaque dark brown aqueous product mixture through a 2.7 $m^2$ spiral wound GE UF membrane having a molecular weight cut-off (MWCO) of 1000 available from GE Water & Process Technologies, Inc. After 4.25 minutes, the collected permeate was analyzed by HPLC. Fructose, glucose, HMF, and intermediates all passed through the membrane while a majority of the colored bodies (humins) did not and remained in the retentate. The collected permeate was a clear orange solution.

In another test, cross-flow nano-filtration was performed by circulating 1 L of the opaque dark brown aqueous product mixture through a 2.7 $m^2$ spiral wound Dairy NF membrane having a MWCO of 150 available from GE Water & Process Technologies, Inc. After 3.8 minutes, the collected permeate was analyzed by HPLC. The permeate consisted of HMF substantially free of fructose, glucose, intermediates, and colored bodies (humins). The collected permeate was a clear pale yellow solution.

In another test, cross-flow filtration was performed by circulating 1 L of the opaque dark brown aqueous product mixture through a 2.6 $m^2$ spiral wound H series membrane having a MWCO of 150-300 available from GE Water & Process Technologies, Inc. After 20.0 minutes, the collected permeate was analyzed by HPLC. The permeate consisted primarily of HMF with a very small amount of fructose and no detectable quantity of glucose or intermediates. The colored bodies (humins) were substantially removed. The collected permeate was a clear pale yellow solution.

When introducing elements of the present invention or the preferred embodiments(s) thereof, the articles "a", "an", "the" and "said" are intended to mean that there are one or more of the elements. The terms "comprising", "including" and "having" are intended to mean that there may be additional elements other than the listed elements.

In view of the above, it will be seen that the several objects of the invention are achieved and other advantageous results attained.

As various changes could be made in the above processes and products without departing from the scope of the invention, it is intended that all matter contained in the above description and shown in the accompanying drawings shall be interpreted as illustrative and not in a limiting sense.

What is claimed is:

1. A process for the production of a product comprising 5-(hydroxymethyl)furfural (HMF) and water, the process comprising:
   combining fructose, water, a homogeneous acid catalyst and at least a first solvent in one or more reaction zones;
   converting in the one or more reaction zones a portion of the fructose to HMF and water;
   removing from at least one of the reaction zones a combination comprising at least a portion of the HMF, humins, homogeneous acid catalyst and first solvent;
   neutralizing the homogeneous acid catalyst by addition of a base to the combination; and
   contacting the neutralized combination with one or more selective membranes to produce a retentate comprising humins and a permeate depleted in humins and comprising HMF.

2. The process of claim 1 wherein the combination further comprises unconverted fructose and intermediates to HMF, the retentate further comprises unconverted fructose and intermediates and the permeate is depleted in unconverted fructose and intermediates.

3. The process of claim 1 wherein the one or more selective membranes are selected from ultra-filtration membranes, nano-filtration membranes, and combinations thereof.

4. The process of claim 3 wherein the one or more selective membranes comprises ultra-filtration membranes.

5. The process of claim 1 wherein the solids content of the combination withdrawn from the reaction zone is reduced prior to contacting the combination with one or more selective membranes.

6. The process of claim 5 wherein the solids content of the combination withdrawn from the reaction zone is reduced by dilution with an aqueous diluent.

7. The process of claim 5 wherein the solids content of the combination withdrawn from the reaction zone is reduced by filtration.

8. The process of claim 5 wherein the solids content of the combination withdrawn from the reaction zone is reduced to less than about 1000 ppm.

9. The process of claim 1 wherein the one or more selective membranes are in a cross-flow arrangement.

10. The process of claim 1 wherein the one or more selective membranes are in a single pass system.

11. The process of claim 1 wherein the one or more selective membranes are in a multi-pass system.

12. The process of claim 1 wherein the one or more selective membranes have a geometry selected from the group consisting of flat, tubular, capillary, and spiral-wound.

13. The process of claim 1 wherein the homogenous acid catalyst is selected from the group consisting of mineral acids, organic acids, and combinations thereof.

14. The process of claim 13 wherein the homogenous acid catalyst is selected from the group consisting of HCl, HBr, HI, $H_2SO_4$, $HNO_3$, $H_3PO_4$, oxalic acid, $CF_3SO_3H$, $CH_3SO_3H$, borontrihalides, and combinations thereof.

15. The process of claim 14 wherein the homogenous acid catalyst is selected from the group consisting of HCl, HBr, $H_2SO_4$, $H_3PO_4$, and combinations thereof.

16. The process of claim 15 wherein the acid catalyst comprises HBr.

17. The process of claim 1 wherein the combination is mono-phasic.

18. A process for the production of a product comprising 5-(hydroxymethyl)furfural (HMF) and water, the process comprising:
   combining fructose, water, an acid catalyst and at least a first solvent in one or more reaction zones;
   converting in the one or more reaction zones a portion of the fructose to HMF and water and to intermediates to HMF;
   removing from at least one of the reaction zones a combination comprising at least a portion of the HMF, unconverted fructose, intermediates, humins, and first solvent,
   contacting the combination with one or more ultra-filtration membranes to produce a retentate comprising humins and a permeate depleted in humins that comprises unconverted fructose, intermediates, HMF, first solvent, and water; and
   contacting the ultra-filtration permeate with one or more nano-filtration membranes to produce a retentate comprising unconverted fructose and a permeate substantially free of unconverted fructose and comprising HMF.

* * * * *